US007399641B2

(12) United States Patent
Nelson et al.

(10) Patent No.: US 7,399,641 B2
(45) Date of Patent: *Jul. 15, 2008

(54) MASS SPECTROMETRIC IMMUNOASSAY

(75) Inventors: Randall W. Nelson, Phoenix, AZ (US); Peter Williams, Phoenix, AZ (US); Jennifer Reeve Krone, Granbury, TX (US)

(73) Assignee: Intrinsic Bioprobes, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/904,467

(22) Filed: Nov. 11, 2004

(65) Prior Publication Data

US 2005/0170526 A1 Aug. 4, 2005

Related U.S. Application Data

(60) Division of application No. 09/524,422, filed on Mar. 11, 2000, now abandoned, which is a continuation of application No. 09/024,988, filed on Feb. 17, 1998, now abandoned, which is a continuation of application No. 08/449,903, filed on May 23, 1995, now abandoned.

(51) Int. Cl.
*G01N 24/00* (2006.01)

(52) U.S. Cl. ....................... 436/173; 435/7.1; 435/7.92; 436/518; 436/524

(58) Field of Classification Search ..................... 435/6, 435/7.1, 7.92, 971, 973; 436/501, 518, 523, 436/524, 173–175, 177, 824, 825
See application file for complete search history.

(56) References Cited

U.S. PATENT DOCUMENTS

| | | | | |
|---|---|---|---|---|
| 4,990,458 | A * | 2/1991 | Rosenfeld | 436/174 |
| 5,042,502 | A | 8/1991 | Guirguis | |
| 5,079,170 | A | 1/1992 | Rosman et al. | |
| 5,171,537 | A | 12/1992 | Wainwright et al. | |
| 5,403,745 | A | 4/1995 | Ollington et al. | |
| 5,437,979 | A * | 8/1995 | Rampal et al. | 435/6 |
| 5,595,653 | A | 1/1997 | Good | |
| 5,719,060 | A * | 2/1998 | Hutchens et al. | 436/174 |
| 5,833,927 | A | 11/1998 | Raybuck et al. | |

FOREIGN PATENT DOCUMENTS

WO WO 94/20831 9/1994

OTHER PUBLICATIONS

Mock et al., Sample Immobilization Protocols for Matrix-assisted Laser-desorption Mass Spectrometery, Rapid Communications in Mass Spectrometry, vol., 6, 233-238, 1992.*

Awata et al., Immunoaffinity Extraction of 4-Hydroxy-2-(4-methylphenyl)benzothiazole and its Metabolites for Determination by Gas Chromatography-Mass Spectrometry, Biol. Pharm, Bull. 17(6) 843-845 1994).*

Bieber, et al., Mass Spectrometric Immunoassay, Analytical Chemistry, Apr. 1995, 67, 1153-1158.

* cited by examiner

*Primary Examiner*—Long V. Le
*Assistant Examiner*—Gary W Counts
(74) *Attorney, Agent, or Firm*—Snell & Wilmer L.L.P.

(57) ABSTRACT

Rapid mass spectrometric immunoassay methods for detecting and/or quantifying antibody and antigen analytes utilizing affinity capture to isolate the analytes and internal reference species (for quantification) followed by mass spectrometric analysis of the isolated analyte/internal reference species. Quantification is obtained by normalizing and calibrating obtained mass spectrum against the mass spectrum obtained for an antibody/antigen of known concentration.

3 Claims, 14 Drawing Sheets

MASS SPECTROMETRIC IMMUNOASSAY

CROSS-REFERENCE TO RELATED APPLICATIONS

This application is a divisional application of Ser. No. 09/524,422 filed on Mar. 11, 2000, now abandoned, which is a continuation of application Ser. No. 09/024,988 filed on Feb. 17, 1998 now abandoned, which was a continuation of original application Ser. No. 08/449,903, which was filed on May 23, 1995, now abandoned.

Financial Assistance for some of the work reported herein was provided by the United States Department of Energy under Grant number DEFG02-91 ER61127. The United States government may have certain rights to this invention.

INTRODUCTION

The present invention relates to a new and useful immunoassay and more specifically to new and improved mass spectrometric immunoassay processes for the detection and/or quantification of one or more antigens or antibodies in a single determining immunoassay. Hereinafter, singular terms are intended to include plural.

BACKGROUND OF INVENTION

Immunoassay techniques first came into wide usage with the development of radioimmunoassay (RIA) in which the specificity of antigen-antibody binding was coupled with the high sensitivity of nuclear particle detection to detect and quantify antibody-antigen binding in the presence of a large background of non-specific material. Later, enzyme immunoassay (EIA) and enzyme-linked immunosorbent assay (ELISA) immunoassays coupled the specificity of antigen-antibody binding with the sensitivity of enzyme chemical reactions to detect and quantify an antigen-antibody binding by producing colored, fluorescent, bio- or chemiluminescent chromophore. EIA and ELISA exhibited an amplification factor as high as $10^8$, allowing sensitivities competitive with RIA without the disadvantages of radioactivity.

Typical ELISA diagnostics relied on an antigen having at least one epitope to which an enzyme-linked antibody could bind with a high affinity. An antigen was affinity-isolated from its biological system and allowed to interact with the enzyme-linked antibody. The enzyme of choice was generally alkaline phosphatase or horseradish peroxidase, both of which generated a colored product upon digestion of appropriate substrates. Although detection of attomole levels of an enzyme has been demonstrated, so that it was, in principle, possible to detect attomole levels of an antigen, traditional immunoassays did not operate at that level of detection because all were limited by non-specific binding of the enzyme-linked antibody to surfaces in the reaction well or vial. This produced a background response which restricted the detection limit of the technique which could not be discriminated against because detection was indirect.

A further limitation of the traditional immunoassays employing optical detection was caused by the limited number of clearly resolvable colored enzyme products, at most two or three, which limited the possibility for an immunoassay to screen for multiple antigens in a single sample. Multiple antigen immunoassays usually focused on a number of separate immunoassays in an array of well plates each requiring its own sample which clearly reduced the utility of this approach. The ideal multi-antigen immunoassay would detect a large number of discrete antigens with high specificity in a single specimen, would cover a large dynamic range, be quantifiable over that range, and could be performed rapidly, that is, in minutes rather than hours, for critical clinical situations and high general throughput.

The sensitivity of EIA and ELISA relied on the specificity of the affinants used to bind with the antigen or antibody being detected. Expensive and hard to produce monoclonal antibodies were usually the reagent of choice because the specificity of monoclonal antibodies is very high. Polyclonal antibodies whose specificity is low could be used in theory but were not a practical choice for a reagent because polyclonal antibodies bind with several species of antigens making the detection of the resulting antibody-antigen complex less specific for a single given antigen species.

Yet another restriction to EIA and ELISA is that they required the antigen-antibody binding to reach an equilibrium for quantification, making the immunoassay take several hours to perform.

Until about 1988, mass spectrometry of proteins and peptides was thought difficult or impossible. At that time Karas and Hillenkamp (Analytical Chemistry, vol. 60, pp. 2299-2301, 1988) demonstrated that proteins could be ejected into the gas phase by embedding them into an organic matrix which was then literally exploded using a pulsed laser beam. This technique is commonly referred to as matrix-assisted laser desorption/ionization (MALDI). When MALDI was coupled to a time-of-flight (TOF) mass spectrometer, a new field of biological mass spectrometry was opened.

While the new MALDI techniques opened the field of biomolecular mass spectrometry, the mass spectrometric analysis of complex biological materials was not possible because of matrix overloading. Recently, Hutchens et al. (Hutchens, T. W. and Yip, T., Rapid Communications in Mass Spectrometry, vol 7, 1993, pp. 576-580.) demonstrated the utilization of affinity capture methods to quasi-purify proteins in a specimen prior to MALDI mass spectrometry. By quasi-purifying the specimen being assayed Hutchens et al. effectively overcame the primary limitation of MALDI mass spectrometry, namely, the suppression of ion signal due to overloading of the matrix. They named their technique "surface-enhanced affinity capture mass spectrometry (SEAC)". They further demonstrated their technique by using single stranded DNA which they immobilized on the mass spectrometer probe tip to quasi-isolate the protein lactoferrin from preterm infant urine.

More recently Hutchens, T. W. and Yip, T., in an international patent application which was published 8 Dec. 1994 (WO 94/28418), described a method and apparatus for using affinity capture to improve mass spectrometric characterization of biomolecules.

Presently, there is no mass spectrometric immunoassay which is capable of qualitatively and quantitatively determining the presence of single or multiple antigen or antibody species in a specimen. It is toward the fulfillment of that need that the present invention is directed.

SUMMARY OF INVENTION

The present invention relates generally to the fields of immunoassay and mass spectrometry and more particularly to a new and useful mass spectrometric immunoassay methodology for unequivocally detecting and/or quantifying one or more antigens or antibodies from a specimen within the limits of detection.

The present invention combines and exploits the specificity of antibody-antigen binding and the ability of the mass spectrometer to unequivocally identify molecules in various qualitative and quantitative strategies to analyze one or more antigens or antibodies in a specimen within the limit of detection. Both qualitative and quantitative strategies utilize an antibody or antigen to capture and isolate another antigen or antibody, respectively, from its surroundings, and thereafter mass spectrometrically analyze the isolated antibody or antigen after release from the capturing agent. This specificity of the antibody-antigen reaction coupled with the ability of the mass spectrometer to separate and unequivocally identify the captured and isolated antibody or antigen by its mass-to-charge ratio from other molecules that may accompany it lends two dimensions of specificity to the present invention.

Because detection using mass spectrometry lends an added dimension of unequivocal specificity, the mass spectrometric immunoassay under the present invention is an improvement over existing immunoassays in several ways. First, the present invention does not require monoclonal antibodies as a reagent, polyclonal antibodies produce equally reliable results. Second, radioactive materials are not required at all. Third, the presence of other substances not the subject of the immunoassay do not interfere with either detecting or quantifying the targeted antigen or antibody. Fourth, an accurate multiplex immunoassay clearly detecting and/or quantifying virtually any combination of different antigens or antibodies is possible.

In addition, the rapid ease by which the mass spectrometer can detect an antigen or antibody regardless of whether the antigen-antibody binding has reached equilibrium grants to the present invention an immunoassay that produces results in a short period of time, minutes rather than hours.

An article by Nelson, R., et al., published in Analytical Chemistry, vol. 67, pp 1153-1158, on or about Mar. 31, 1995, describes certain portions of the present invention in detail.

Accordingly it is a prime object of the present invention to provide a new and improved mass spectrometric immunoassay for determining whether one or more designated antigens and/or antibodies are present in a specimen.

A further object of the present invention is to provide a novel and unique immunoassay for determining what specific antigens and/or antibodies are present in a given specimen.

Another object of the present invention is to provide a new and improved immunoassay for determining how much detected antigen or antibody is present in a specimen.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

BRIEF DESCRIPTION OF THE DRAWINGS

In the drawings:

FIG. 4 is a working curve relationship between the concentration of myotoxin a in venom laced human blood samples and the magnitude of mass spectrometric immunoassay responses for myotoxin a, normalized with the modified variant, H-myotoxin a, and demonstrating the working curve quantification strategy for quantifying myotoxin a;

FIG. 5 is a mass spectrum resulting from the mass spectrometric immunoassay of the present invention of a venom laced human blood sample containing four modified variants of myotoxin a, demonstrating the bargraph quantitative strategy for quantifying the antigen, myotoxin a;

FIG. 6 is a mass spectrum resulting from the mass spectrometric immunoassay of the present invention of a venom laced human blood sample containing the modified variant, H-myotoxin a, demonstrating the relative limit signal quantitative strategy for quantifying myotoxin a;

DETAILED DESCRIPTION

Figure 1:
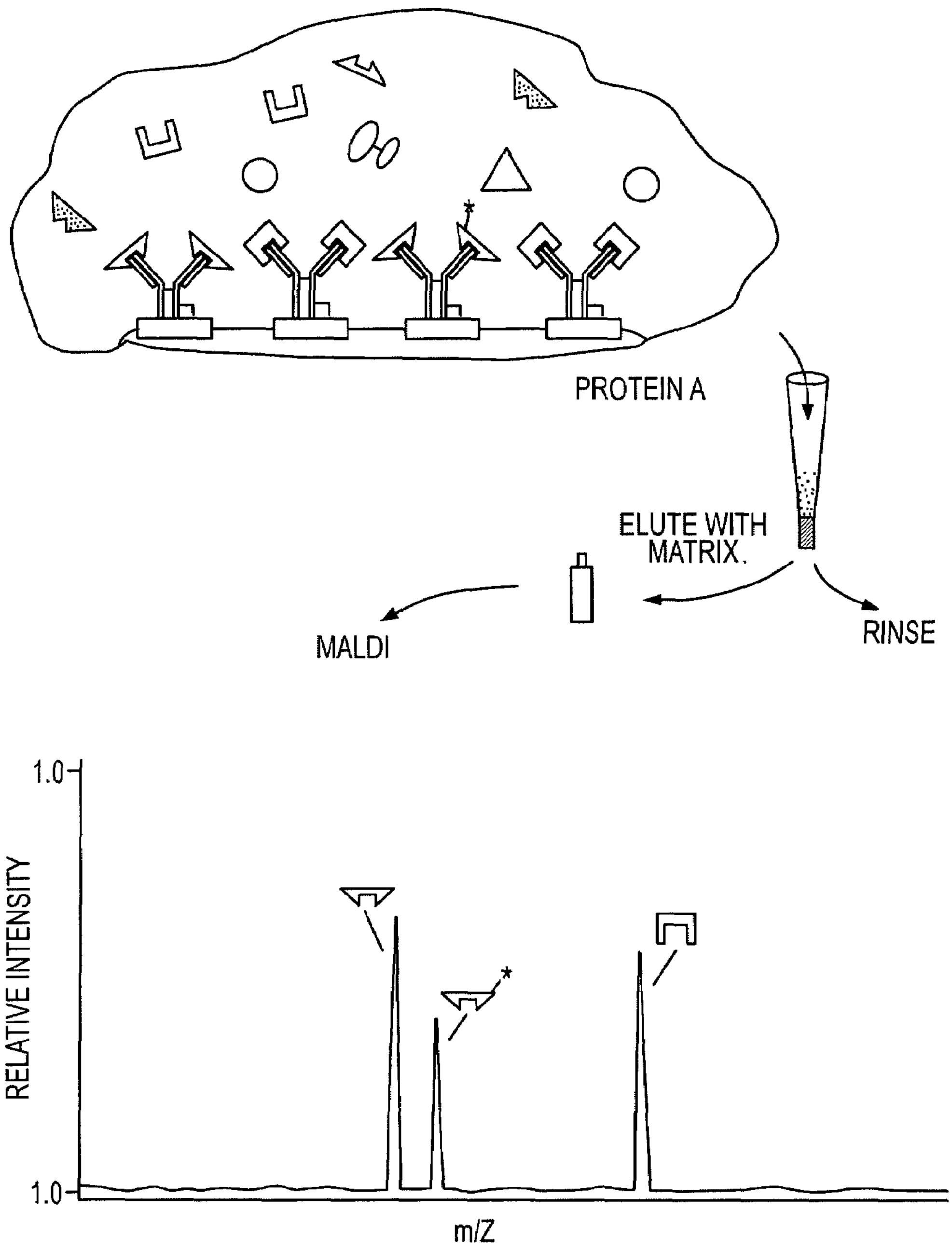
FIG. 1 is a depiction of the general scheme of a multiplex mass spectrometric immunoassay under the present invention showing affinity capture and isolation of two antigen analytes and a modified variant of one of the antigen analytes, denoted with a star, and showing the resulting mass spectrum which distinctly resolves each antigen analyte and modified variant.

The present invention relates to a new mass spectrometric immunoassay and more specifically to new and improved processes for the detection and/or quantification of one or more antigens or antibodies in a single immunoassay.

The present invention can be utilized to detect and/or quantify single or multiple antigens or antibodies in a specimen. Single terms as used herein are meant to include plural.

In its simplest context, the present invention involves two phases: capture and isolation of an antibody analyte or antigen analyte, followed by mass spectrometric analysis of the captured antigen analyte or antibody analyte. The present invention can be used for qualitative and/or quantitative purposes. That is, the present invention can be used to determine whether a certain antibody or antigen is present in a specimen (qualitative), and/or to measure the amount of the antigen or antibody present in a specimen (quantitative).

A more detailed description of the several facets of this invention appears hereafter utilizing the following lexicon.

"Affinant" is the antibody and/or antigen which is used to make the affinity reagent. Usually, an affinity reagent to analyze for antigens will be made with one or several types of antibody.

Similarly, an affinity reagent to analyze for antibodies will be made with one or several different antigens. However, all quantitative analyses in the present invention require the affinity reagent to capture at least two different types of molecule, one of which is the analyte, the other molecule acting as an internal reference species. Sometimes, the analyte may be an antibody and the internal reference species an antigen, or vice versa. Where this is so, it would be necessary for the affinity reagent to contain both an antibody and an antigen. For example, because the number of resolvable types of antibody is small, a protein that is not an antibody may make a useful internal reference species for an antibody, because it has a resolvable mass and a specific antibody is readily available for it. In such a case, the affinity reagent needs to contain an immobilized antibody having a specific affinity for that protein, in addition to an immobilized antigen having a specific affinity for the antibody analyte.

"Affinity" is the ability of a molecule to bind with another molecule having proper fitting conformation.

"Affinity reagent" is a type of antigen or antibody immobilized to a solid substrate. Preferably, immobilization is obtained by covalently linking the antigen or antibody to the solid substrate, although non-covalent linkage may be acceptable. The antibody or antigen can be directly linked to the solid substance surface, or can be indirectly attached to the solid substrate by linking the antibody or antigen to a coating on the solid substrate.

"Allergen" is a particulate material capable of stimulating an allergic response in susceptible individuals. Typically, allergens include dusts, pollens, molds, spores, and particles of insect and animal detrita. Each type of material may carry on its surface, many different kinds of proteins capable of stimulating an allergic response. The allergic response is characterized in the human body by the production of elevated levels of an immunoglobulin, IgE, molecular weight~170,000 Da, which is distinguishable from other immunoglobulins such as IgG which have a different molecular weight (IgG:~150,000 Da).

"Analyte" except as otherwise defined, is an antibody or antigen that is captured, isolated and mass spectrometrically analyzed for the qualitative purpose of detecting whether a specimen contains a certain antibody or certain antigen. Depending on the qualitative method employed, the analyte may be the certain antibody or certain antigen being looked for in the specimen, or may be another antibody or antigen used to indirectly detect the certain antibody or certain antigen.

"Antibody" is a protein that specifically binds with another molecule that possesses one or more unique antigenic sites.

"Antigen" is any molecule having an antigenic site that can bind to an antibody. It is apparent that the categories of molecules that may be considered antigens under this definition is broad, essentially any molecule that can bind with an antibody qualifies as an antigen including an allergen.

"Counterpart" when used to describe an antibody or antigen, is an antibody or antigen which has a molecular weight indistinguishable in the mass spectrum from that of the analyte, and which gives a response identical to that of the analyte when both are subjected to mass spectrometric immunoassay from specimens of identical concentration.

"Disassociation agent" is any active cause which disassociates or unbinds a captured analyte from the affinity reagent. A laser desorption/ionization agent may also act as a disassociation agent. Examples of a disassociation agent include but are not limited to: addition of a buffer solution, heating, sonication, application of an electric potential, or addition of a MALDI matrix.

"Effective amount" of affinity reagent is that amount necessary to capture an adequate quantity of the analyte (and internal reference species where relevant) to achieve the desired result.

"Internal reference species" is an antibody or antigen whose specific affinity for another antibody or antigen is exploited in the mass spectrometric immunoassay for quantitative purposes. The internal reference species is captured, isolated and mass spectrometrically analyzed alongside the analyte.

"Laser desorption/ionization agent" is any active cause which enables an analyte to be laser desorped/ionized. An example of a laser desorption/ionization agent is the addition of a MALDI matrix.

"Mass spectrometrically analyzed" is analyzing the antigen analyte or antibody analyte with a mass spectrometer resulting in a mass spectrometric response. Generally, a mass spectrometer is an instrument designed to determine the mass-to-charge ratio of ions. For this process, it is necessary for the analyte molecules to be volatilized, and ionized. The ionized molecules are then accelerated by an electric field into the analyzing device, which separates the ions by virtue of a property dependent on the mass-to-charge ratio (m/z). Among these properties are: deflection in a magnetic field, velocity after acceleration through a fixed electric potential drop, cyclotron orbital frequency in a magnetic field, and trajectory in a radio frequency quadrupole field. Because antigens and antibodies are usually relatively large molecules and cannot be volatilized under ordinary mass spectrometric procedures, volatilization and ionization of the antibody or antigen usually involves some kind of assistance. One common procedure of assistance is known as matrix-assisted laser desorption/ionization, or MALDI. Therefore, "mass spectrometric analysis" is intended to include techniques that assist the mass spectrometer in volatilizing and ionizing the antibody or antigen molecules when such assistance is needed.

"Mass spectrometric mixture" is a mixture containing an antibody or antigen which can be laser desorped/ionized by a mass spectrometer.

"Mass spectrometric response" (or "Response") is the response received from a mass spectrometer indicating whether or when an ion struck the mass spectrometer's detector and whether or when no ion struck the detector. A non-zero response at a given mass-to-charge ratio indicates that the material mass spectrometrically analyzed contained a given molecule that gave rise to the ion corresponding to the response at that charge-to mass ratio. It is apparent that a zero mass spectrometric response would indicate that the material mass spectrometrically analyzed either did not contain that molecule, or contained that molecule in levels below the limit of detection.

It is important to realize that the mass spectrometric response is defined as a change in the level of the signal measured at the mass spectrometer detector, not simply the absolute level of that signal. In some types of mass spectrometer, and particularly in matrix-assisted laser desorption/ionization time-of-flight mass spectrometers, there is a detectable signal, resulting in a non-zero baseline, throughout the mass spectrum arising from such causes as background noise and the arrival of ions at the detector at times non-specific to their mass/charge ratio. Thus, the mass spectrometric response for an ion species at a specific mass/charge ratio is defined as the change in the mass spectrometer signal above this baseline signal level.

Detection of an ion at a given setting of electric and magnetic field strengths, or at a given time after the ion is accelerated, is controlled by the mass-to-charge (mass/charge) ratio of that ion thereby providing an accurate means of identifying the molecule that gave rise to that ion by the molecule's mass-to-charge ratio. The number of ions that strike the detector at a given setting, or at a given time, is indicated by the magnitude of the mass spectrometric response. A "mass spectrum" is a collection of mass spectrometric responses over a range of mass-to-charge ratios.

A mass spectrum is commonly expressed graphically in terms of relative "intensity", against mass-to-charge ratio (m/z). Where an ion arises from a molecule present in the material being mass spectrometrically analyzed at or above the limit of detection, the response is expressed as mass spectral signals or peaks (signal, or peak) at the relative mass-to-charge ratio of the ion. Where the ion charge is +1, the mass-to-charge ratio for that ion is equivalent to the molecular weight of the ion. Molecular weight is expressed in Daltons (Da.) and may be used interchangeably with the term mass-to-charge ratio for singly charged ions.

The magnitude of a mass spectrometric response can be measured in terms of "intensity", height of the response, or "integral", the area under the response. It is apparent that mass spectrometric response can be expressed in a variety of tangible and intangible forms including but not limited to signals, charts, electronic data and electric currents. A zero response, a response without magnitude, at a given mass-to-charge ratio indicates the material being mass spectrometrically analyzed either did not contain a molecule that could give rise to an ion of the given mass-to-charge ratio, or did not contain that molecule at a level at or above the level of detection.

"Modified variant" is an internal reference species which is made from an antibody or antigen analyte or a counterpart thereof, has affinity for the same antigen or antibody as does the analyte, and produces a mass spectrometric response relative to the analyte which is fixed and readily determinable, but has a different molecular weight such that it is resolvable in the mass spectrum from the analyte.

"Non-specific affinity" is the strongly attractive interaction with a broad range of antibody or antigen species. By way of example only, the substance Protein A has a strong affinity for all antibodies of the IgG family.

"Normalize" or any form of the word, is that procedure for correcting mass spectra for differences in instrument performance during mass spectrometric immunoassay of multiple analytical systems. In essence, normalization provides for accurate results when two immunoassays are compared in the quantitative strategies of the present invention. Normalization is preferably achieved with the assistance of an internal reference species, but conceivably can be achieved without the assistance of an internal reference species if instrument parameters are carefully controlled so as to be identical in the mass spectrometric immunoassay of multiple analytical systems. Alternatively, if the dependence on the instrument parameters of the mass spectrometric response to a given analyte concentration is sufficiently well known, the mass spectrometric response may be corrected for the effects of changing instrument parameters.

"Post-combination affinity reagent" is an affinity reagent which has been allowed to bind with its target antigen or antibody.

"Preparation" is an operator created substance or material and used for a particular purpose in the mass spectrometric immunoassay. The term is used to distinguish it from the specimen. Under one method of the present invention, material containing a counterpart antigen is created for the purpose of determining whether a certain antibody species is present in a specimen, such as antiserum, and is termed the "preparation" to distinguish it from the specimen and avoid confusion in describing the method. Under several quantitative methods, a material containing a counterpart antigen or antibody is created and termed the "preparation" and used in the quantification methods.

"Solid substrate" is defined as any physically separable solid to which an antibody or antigen can be directly or indirectly attached including but not limited to agarose beads, nylon, metals, glass, silicon, and organic membranes.

"Specific affinity" is the strongly attractive interaction between specific antigens and their corresponding antibodies. The selective attraction between an antigen and its corresponding antibody occurs between the antigenic site, or epitope, of the antigen and a recognition region in the antibody. As such, it may be possible to modify an antigen by altering its molecular weight, without noticeably altering the epitope, so that the modified antigen also has a specific affinity for the same antibody as the unmodified antigen. An antibody may similarly be modified without eliminating its specific affinity for its antigen. The high specific affinity between antigens and antibodies is the key to the selective capture and isolation of a specified antigen or antibody in an immunoassay.

"Specimen" is any material which is the focus of the mass spectrometric immunoassay. Frequently the specimen will be of biological origin, for example a blood sample, and contain analytes that are similarly of biological origin, for example peptides, proteins and antibodies. However, it is possible that the specimen may be non-biological in origin, for example a groundwater specimen, and the analyte similarly may be of non-biological origin, for example a pesticide. All that is necessary for a successful immunoassay is that it should be possible to prepare an antibody having a specific affinity for that analyte.

"Unbound remainder" is whatever is left after the affinity reagent screens the specimen.

The "mass spectrometrically immunoassay" is that procedure in which a specimen is incubated with an affinity reagent which will specifically capture an analyte, for a time sufficient for the affinity reagent to bind a detectable fraction of the analyte, creating a post-combination affinity reagent. The post-combination affinity reagent is then separated from the unbound remainder of the specimen sample to isolate the captured antigen from the unbound remainder. Preferably, the isolated post combination affinity reagent is then washed to remove any unbound remainder adhering to the isolated affinity reagent.

A laser desorption/ionization agent is then added to isolated post combination affinity reagent to unbind any antigen bound to the affinant and form a mass spectrometric mixture from which the unbound antigen is then mass spectrometrically analyzed. If the specimen contained the certain antigen at a level above the detection limit of the mass spectrometric immunoassay process for that antigen, the resulting mass spectrum will show a mass spectral signal at the unique mass-to-charge ratio of the certain antigen. If the specimen did not contain the certain antigen at a level above the detection limit of the mass spectrometric immunoassay process for that antigen, no such signal will be evident.

Such a mass spectrometric immunoassay procedure can result in a qualitative or a quantitative analysis, depending on whether or not a quantification method is used.

A multitude of qualitative and quantitative methods are possible using the present invention. Below three qualitative methods are discussed in detail, followed by a detailed discussion of six quantification methods. The mass spectrometric immunoassay of the present invention is very sensitive and requires only very small quantities of analyte and/or small volumes of analyte containing samples. The detection limit is approximately between $1\times10^{9}$ and $1\times10^{10}$ analyte molecules in about 200 μL (microliters) of sample.

The first qualitative strategy is designed to determine whether one or more antigens are present in or are absent from a specimen. Antibodies to each antigen to be detected are immobilized on a solid substrate creating the affinity reagent. The affinity reagent is then incubated with the specimen to screen the specimen for any antigen present in the specimen that has an affinity for the affinant-antibody immobilized on the affinity reagent. Screening in this context means to combine the specimen and affinity reagent for enough time to allow the affinant-antibody to combine with a detectable amount of antigen for which it has a specific affinity. The affinity reagent will capture some or all of the antigen present in the specimen, if any. The post-combination affinity reagent is then separated from the unbound remainder of the specimen to isolate the captured antigen from the unbound remainder. Preferably, the isolated post-combination affinity reagent is then washed to remove any unbound remainder adhering to the isolated affinity reagent.

A disassociation agent is applied to the post-combination affinity reagent to disrupt the antibody-antigen binding and produce a solution containing free antigen which can be separated from the solid affinity reagent by filtering. If the mass spectrometric analysis is to be performed using matrix-assisted laser desorption/ionization (MALDI), the sample must be combined with an excess amount of a laser desorption/ionization agent (known otherwise as a "MALDI matrix") and allowed to crystallize by drying. In general the MALDI matrix materials which are effective laser desorption/ionization agents are also remarkably effective disassociation agents, and disassociation using these materials is preferred, in particular because the process of disassociation and creation of a mass spectrometric mixture is thereby made simple and rapid.

The solution resulting from the disassociation step may be mass spectrometrically analyzed. If the solution is to be analyzed using matrix-assisted laser desorption/ionization mass spectrometry, it must first be combined with a MALDI matrix if such a matrix material was not used as a disassociation agent. If the specimen contained one or more of the antigen species for which the affinity reagent has a specific affinity, at a level above the detection limit of the mass spectrometric immunoassay process for that antigen, the resulting mass spectrum will show a mass spectral signal at the unique mass-to-charge ratio of the certain antigen. If the specimen did not contain the certain antigen at a level above the detection limit of the mass spectrometric immunoassay process for that antigen, no such signal will be evident. This strategy may be used to screen specimens for as many discrete antigen species as can be distinguished from each other in a single mass spectrum. In the event that more antigens must be searched for than can be distinguished in a single mass spectrum, two or more affinity reagents must be created, each having affinities to different sets of distinguishable antigens.

The procedures for the second qualitative strategy under the present invention are similar to the first except the affinity reagent is made with antigens seeking antibodies. The analyte is an antibody. The same general protocols apply. An antigen known to have a specific affinity for the antibody analyte is immobilized to a solid substrate. The affinity reagent is incubated with the specimen being assayed for the desired antibody and allowed to capture the antibody for which it has a specific affinity. After washing the reagent any captured antibody is isolated from the specimen environment. A disassociation agent then a laser desorption/ionization is added to the isolated antibody to free it from the substrate and facilitate ionization prior to mass spectrometric analysis. Alternately, only the laser desorption/ionization agent can be added without the disassociation agent to the isolated antibody analyte. A mass spectral response at the molecular weight (same as single charged m/z) of the target antibody evidences the presence of the antibody in the specimen.

In addition to using pure antigens to capture specific antibodies, it can also be useful to use impure antigens to capture classes of antibodies. Such a situation arises in testing for allergies, in which whole allergen particles, such as dusts, pollens, molds, spores and particles of insect and animal detrita, may be covalently anchored to a solid substrate, or even used without such anchoring if the particles are sufficiently large to be separated by filtering may be used to search for elevated levels of an antibody, IgE, which is produced as part of the allergic response. IgE has a molecular weight of ~170,000 Da, sufficiently different from that of IgG, another major antigenic antibody class with a molecular weight~150,000 Da, that IgE and IgG are distinguishable in a mass spectrometer. However, like other antibodies, individual types of IgE molecules are not resolvable from each other. Accordingly, determination of which of several possible allergens has a specific affinity for IgE in a blood sample would necessarily use a single species of allergen, for example, the pollen of a specific plant, such as ragweed, to screen a specimen for IgE characteristic of allergy to ragweed pollen, and separate screening procedures would be carried out for each specific allergen. Small molecules, such as drugs, do not stimulate an allergic response when present alone, but do so effectively when bound to proteins to form conjugates. Screening for life-threatening sensitivity to drugs therefore would necessarily use affinity reagents in which the drug molecules in question were attached to proteins incorporated in the affinity reagent.

The advantage of such screening over the conventional skin and patch tests for allergy is not only its enhanced speed but, equally important, the ability to avoid a potentially catastrophic hyperallergenic reaction that could occur when the patient is used as an allergy detector.

Because antibodies within a certain class, such as immunoglobulin G (IgG) do not vary in molecular weight by a sufficient amount to be distinguishable mass spectrometrically, a different strategy must be adopted to screen a specimen for specific types of similar antibodies, for example, antibodies belonging to the IgG class. In this strategy detection of a specific antibody is indirect. A specimen is combined with a solid substrate having a broad non-specific affinity for antibodies. A representative sample of the antibody population in the specimen will bind with the solid substrate creating an affinity reagent. The affinity reagent is then incubated with a screening preparation made with an antigen or antigens known to have a specific affinity for the antibody or antibodies to be searched for. If a certain antibody is a member of the antibody population on the affinity reagent, and the specific antigen to that antibody is present in the screening preparation, then that antibody will capture its specific known antigen from the preparation. The affinity reagent is then separated from the preparation leaving behind the unbound remainder. Preferably, the isolated affinity reagent is washed to remove any unbound remainder adhering thereto.

A laser desorption/ionization agent is then applied to the isolated affinity reagent to unbind any antigen bound to the affinant-antibody forming a mass spectrometric mixture from which the unbound antigen is then mass spectrometrically analyzed. A mass spectral signal at the unique mass-to-charge ratio of a known antigen indicates the antibody specific for that antigen was present in the specimen. Absence of a mass spectral signal indicates that the certain antibody was not present in the specimen at or above the detectable limit.

The preferred incubation method for all three qualitative methods is arrived at empirically and depends on the given analytical system. Generally, incubation can be stationary (combining the affinity reagent and sample then agitating), flowing (one-time or repetitive flowing of sample over the affinity reagent), or accelerated by the application of an electrical potential across the sample solution. Because the use of an internal reference species serves to calibrate variables in the incubation process as well as in the mass spectrometric analysis, it is not necessary to ensure that incubation proceeds to equilibrium to achieve accurate analyses. Rapid incubations and consequently rapid analyses are therefore possible under the present invention.

Preferably, the disassociation agent and laser desorption/ionization agent chosen is arrived at empirically, however, the preferred agent is often the addition of any material commonly referred to as a "MALDI matrix" by those in the field of mass spectrometry. Examples of commonly used MALDI matrix materials can be found in: Fan Xiang and Ronald C. Beavis, Rapid Communications in Mass Spectrometry, vol. 8, pp. 199-204, 1994 and in Ronald C. Beavis, Organic Mass Spectrometry, vol. 27, pp. 653-659, 1992.

Because an unbound antigen analyte or unbound antibody analyte is typically too large a molecule to be ionized, the unbound analyte cannot ordinarily be mass spectrally analyzed without additional preparatory techniques. Preferably, matrix assisted laser desorption/ionization (MALDI) techniques enable mass spectrometric analysis of the analyte. Standard MALDI protocols can be found in Ronald C. Beavis, Organic Mass Spectrometry, vol. 27, pp. 653-659, 1992.

The mass spectrometer used in the present invention can be any mass spectrometer that will analyze the analytes including a magnetic sector mass spectrometer, a Fourier transform ion cyclotron resonance (FTICR) mass spectrometer, a quadrupole ion trap mass spectrometer and any time-of-flight (TOF) mass spectrometer. Of these the TOF mass spectrometer is preferred.

Mass spectrometric analysis of the captured, isolated and unbound analyte results in an analyte mass spectral signal at the mass-to-charge ratio characteristic of the analyte. The location of the signal on the mass spectrum is dependent on the molecular weight of the analyte, thereby providing a reliable means for identifying the analyte. The mass spectral signal also has magnitude. The magnitude of the signal is indicative of the amount of analyte that is ionized and detected by the mass spectrometer. Mass spectrometric signal magnitude has at least two dimensions that are directly measurable, intensity or height of the signal, and integral or the area under the signal. Either the intensity or the integral can be used to quantify.

The mass spectrometric immunoassay process can also be designed to quantify an antibody or antigen present in a specimen. All such quantitative analyses utilize standard preparations containing known concentrations of the analyte for calibration. In addition, because it is difficult to control the analytical conditions sufficiently well to ensure a constant absolute mass spectrometric response for a constant analyte concentration in different samples, quantitative analysis using the present invention relies on the presence of or the introduction of at least one internal reference species in the analytical system prior to incubation with the affinity reagent. The internal reference species can be added to the analytical system being assayed, or be intrinsic thereto. It is captured, isolated and mass spectrometrically analyzed simultaneously with the analyte, thereby serving to calibrate the analytical conditions from one analysis to another because both analyte and internal reference species respond identically to changes in these conditions.

The affinity reagent must contain an affinant that will specifically capture or bind with the internal reference species. It is essential that the internal reference species have a molecular weight sufficiently different from that of the analyte or analytes that it can be resolved in the mass spectrum from the signals arising from the analyte or analytes. However, the molecular weight difference is preferably the minimum necessary for resolution in the mass spectrum, because analytes differing very greatly in mass may not respond identically to changes in the mass spectrometer operating conditions. Preferably, the internal reference species is a modified variant of the analyte. Where a modified variant is used as the internal reference species, an affinant that can capture the analyte can usually also capture the modified variant because the modification shifts the molecular weight of the antibody or antigen without destroying its affinity. Where the internal reference species is not a modified variant of the analyte, another immunochemical affinity group must be present in the affinity reagent in order to simultaneously capture and isolate that internal reference species alongside the analyte. It is possible, and may be desirable, for a protein that is not an antibody to be used as an internal reference standard in an analysis of an antibody species. In such a situation, the affinity reagent would be prepared with two classes of molecules, an antibody specific for the protein and an antigen for which the analyte is specific.

The number of internal reference species employed also depends on the quantification method employed. The working curve or single point quantification approaches require at least one internal reference species present in the analytical system. The bargraph quantification approach requires several internal reference species.

The internal reference species in a quantification method serves two roles: 1) the role of a normalizer, and 2) the role of a concentration indicator. There is more than one possible strategy or method for quantification of an antigen or antibody under each of these roles.

The internal reference species serves to correct for differences in affinity reagent activity or concentration, for differences in incubation times for different samples, and for differences in mass spectrometer performance during the mass spectrometric immunoassay of multiple samples, thereby ensuring accurate quantification. However, because all mass spectrometric responses are thereby determined relative to the internal reference species response, this internal reference species signal also serves as a concentration indicator, that is, the internal reference species signal for a given concentration of that species is calibrated by various strategies so as to indicate a given concentration of the analyte species.

Quantification strategies all involve mass spectrometric immunoassay of at least two separate analytical systems. In most of the quantitative strategies, one analytical system contains the specimen, and the other a preparation containing the antibody or antigen analyte or a counterpart thereof in known concentration, or in a concentration which has been altered by a known amount by adding a known amount of the analyte where both the specimen and the preparation contain the same internal reference species in known concentration, preferably the same.

Normalizing with an internal reference species can be accomplished in two basic ways, that is, during mass spectrometric analysis or after. Both methods require the analytical samples to contain the same internal reference species. For normalizing during mass spectrometric analyses, the mass spectrometer is adjusted so as to bring the internal reference species signals of each immunoassay to a value proportional to the concentration of the internal reference species. Most conveniently, the internal reference species concentrations in all the analytical samples are the same, and the mass spectrometer is adjusted to bring all internal reference species signals to the same value. For normalizing after mass spectrometric analyses, the mass spectrum for each assay is divided or multiplied by an appropriate factor, again to bring the internal reference species mass spectral responses to a value proportional to the concentration of the internal reference species. The second procedure is preferred. The result is to normalize all mass spectral responses or signals, and all affinity capture procedures to one standard thereby artificially, or in practice, making instrument performance and affinity capture procedures in each of the immunoassays the same. The working curve strategy, standard addition strategy, single point calibration strategy, and the bargraph strategy are all quantification strategies under the present invention that employ one or more internal reference species as both a normalizer and a concentration indicator.

Although it is preferred that the normalization of mass spectra be achieved where the internal reference species concentration in each analytical sample being mass spectrometrically assayed is the same in each analytical sample, it is possible to normalize multiple mass spectra with analytical samples containing the same internal reference species in different, but known concentrations. To normalize under these conditions a scale is determined for the magnitude of that internal reference species mass spectral response and that scale is used to normalize the other mass spectra. By way of illustration only, suppose sample A contains the internal reference species, I-A, in concentration of 100, and sample B contains the same internal reference species, termed I-B to distinguish from A's internal reference species, in concentration of 50. After mass spectrometric immunoassay of A and B, the mass spectral signal for I-A is adjusted to fit an intensity of one (normalized intensity), the other mass spectral signals in A's mass spectrum are also adjusted so as to be in the same original proportion (in intensity) to the adjusted I-A signal as they were for the initial I-A signal. Because the concentration of I-B is half the concentration of I-A, the mass spectral signal for I-B then adjusted to fit a normalized intensity of 0.5. The other mass spectral signals in B's spectrum are also adjusted so as to be in the same original proportion (in intensity) to the adjusted I-B signal as they were for the initial I-B signal. Preferably, all spectra adjustments are accomplished with the aid of computer data manipulation software such as LAB-CALC, produced by Galactic Industries, Salem, N.H.

For accurate normalization and/or calibration using an internal reference species the absolute amplitudes of the mass spectrometric signals for the analyte and internal reference species should be similar. If these two signals differ by a large factor, for example by a factor of several hundred, it will not be possible to measure both signals accurately in the same mass spectrum because the detection system cannot respond accurately to signals differing by so large a factor, i.e., the dynamic range is limited. For example, in the time-of-flight mass spectrometers which are the preferred devices for obtaining mass spectra of laser-desorped ions in the present invention, the signal from the mass spectrometer must typically be digitized, that is, converted to a binary number suitable for transfer to a computer memory, at successive time intervals as short as 5-10 nanoseconds. The digitization circuitry typically converts the signal to a binary number having a value between 0 and 256. If a 1 volt signal, for example, corresponded to the digital value of 256, then all signals larger than 1 volt would also be registered as 256 and the system would have no ability to measure any such signals accurately. Conversely, in the absence of any electronic noise, all signals lower than 1/256 volts would be registered as 0 and again the measurement would be inaccurate. Low signals above 1/256 volt are also measured inaccurately because the binary scale is coarse and because of noise effects. Preferably, the absolute amplitudes of the mass spectrometric signals for the analyte and internal reference species should differ by less than a factor of ten, and the mass spectrometer is adjusted to bring the more intense signal near the allowable maximum.

The mass spectral signal of an internal reference species is typically used to directly quantify an analyte by comparing the internal reference species signal to the analyte signal, after the internal reference species signal has been calibrated by a working curve or standard addition approach.

It is apparent that given the high specificity of affinity capture and isolation, and of mass spectrometry, quantification strategies can be employed to quantify multiple antigens or antibodies in the same specimen. It is also apparent that it is possible to employ multiple quantification strategies in a given assay to quantify single or multiple antibodies or antigens.

DETAILED QUANTIFICATION METHODS USING THE FIRST AND SECOND QUALITATIVE MASS SPECTROMETRIC METHODS

Below is a detailed description of each of the quantification strategies as employed with the first and second qualitative mass spectrometric immunoassay methods.

It is apparent that, because analytical parameters may vary, including differences in affinity reagent activity or concentration, differences in incubation times for different samples, differences in elution efficiency, and differences in mass spectrometer performance during the mass spectrometric immunoassay of multiple specimens, therefore the absolute intensity of the mass spectrometric response for a given analyte in a given analysis cannot be used to derive a concentration for that analyte. Instead, an internal reference species (IRS), which is preferably captured by the same affinity reagent during the same incubation time, eluted under identical conditions and mass spectrometrically analyzed under identical conditions, serves to calibrate all of these variables at one time. All analyte signals are therefore determined as ratios to the respective IRS signals. When this is done it is possible also to calibrate the analysis by determining the analyte/IRS signal ratio for a known concentration ratio of analyte and IRS in an analytical sample. The methods for accomplishing this calibration are known as the working curve approach, the standard addition approach, and the single point calibration approach, and are used here exactly as in standard analytical chemistry procedures.

The working curve approach is developed in anticipation of the fact that generally the analyte concentration encountered in an analysis will not be identical to the analyte concentration used to calibrate the IRS signal. There are two possible approaches.

a) It may be assumed that the relationship between analyte/IRS concentration ratio and analyte/IRS signal ratio is accurately linear. Then, for example, if the analyte/IRS signal ratio is 2:1 for equal concentrations of analyte and IRS, an analyte/IRS signal ratio of 4:1 signals an analyte concentration exactly twice the known IRS concentration in the sample. It is usually safe to assume that such a linear assumption may hold, with an accuracy of approximately 10% or better, for analyte/IRS concentration ratios between approximately 1/3 and 3 times the ratio at which the original calibration was performed (i.e., over about a factor of 10 in concentration). When this assumption of linearity is valid, the relationship between analyte concentration and internal reference mass spectrometric response may be determined using a single calibration sample and this approach is known herein as the single point calibration method.

By way of illustration, suppose signal A for analyte A of known concentration 1000 has a magnitude of 10 units, and signal B for analyte B of unknown concentration has a magnitude of 7.2 units, and it is known from prior calibration that equal concentrations of both analytes will yield equal mass spectral signals. In calibrating A's signal, each unit of A's magnitude represents a concentration of 1000/10 or 100. Analyte B's concentration is therefore $7.2\times100$ or 720 units. If equal concentrations of A and B yield different mass spectral responses the calibration must include the ratio of the mass spectral responses. For example, if the mass spectral signal for a given concentration of A were 1/2 the mass spectral signal for the same concentration of B, then the concentration of B corresponding to a signal magnitude of 7.2 units in the above example would be 720/2 units, or 360 units.

For simple ratio quantification of analytes in separate specimens, the specimens (with internal reference species present) are each mass spectrometrically immunoassayed with an affinity reagent having an affinity for each antigen or antibody being looked for in the relevant specimen, and for the internal reference species. The resulting mass spectra are normalized using the internal reference species signals then the signal of the analyte of unknown concentration is calibrated against the signal of the analyte of known concentration as described in the hypothetical example above.

b) For situations where the analyte/IRS concentration ratio is expected to vary over more than a factor of 10, or where the relationship is expected to be non-linear, or where greater accuracy is required, the relationship between analyte/IRS concentration ratio and analyte/IRS signal ratio may be determined over as large a range as desired by making a series of preparations with varying analyte/IRS concentration ratios in which the analyte concentrations span the expected analyte concentration range. The greater the number of preparations, the more accurately the relationship between analyte/IRS signal ratio and analyte concentration will be determined. The antibody or antigen analyte used to make the preparations is generically termed the preparation analyte, or specifically termed the preparation antigen or preparation antibody. The preparations either contain the same internal reference species in the same concentration as the specimen, or a concentration known relative to that in the specimen. After subjecting each sample to mass spectrometric immunoassay, the ratios of the analyte mass spectrometric responses to the corresponding internal reference species mass spectrometric responses are plotted as a function of the known ratios of the analyte/internal reference species concentrations for each sample. The resulting relationship, or working curve, may be expressed in a variety of ways, including, but not limited to, a graph, a mathematical relationship or computerized data.

If the analyte (antigen or antibody) is present in the specimen, as evidenced by an analyte mass spectral signal on the specimen mass spectrum, then the analyte can be quantified by locating the point on the working curve relationship (ultimately a mathematical relationship) appertaining to the magnitude of the analyte/IRS signal ratio and determining the analyte concentration that corresponds to that point, given the known IRS concentration.

As an alternative to the generation of a working curve spanning a wide range of analyte concentrations, over which the working curve relationship might be expected to be non-linear, or for extremely rapid determination of analyte concentrations directly from the mass spectrum, a unique bargraph quantification method may be used. The bargraph quantification method requires the presence of several distinct internal reference species in the analytical sample, each at a different and known concentration and differing in mass from the certain antigen or antibody and each other sufficiently to be distinguishable in the mass spectrum. Because the concentrations of the internal reference species must be known, the internal reference species are typically added to the specimen, not intrinsic thereto. Mass spectrometric immunoassay of the specimen is then executed using an affinity reagent having specific affinity for each internal reference species and for the certain antibody or certain antigen being looked for in the specimen. The resulting mass spectrum will contain a mass spectral signal for each internal reference species and a mass spectral signal for the certain antigen or certain antibody, if present.

Preferably, the internal reference species are all modified variants of the analyte being mass spectrometrically immunoassayed so that the internal reference species are capable of being captured by a single affinant, and the mass spectral signals all neighbor one another on the mass spectrum. Each distinct internal reference species must have a molecular weight sufficiently different from the other internal reference species so as to be resolvable in a single mass spectrum. In addition, it is preferable that the range of concentrations covered by the internal reference species span the concentration range in which the analyte is reasonably expected to be found. It is not necessary that the different internal reference species be captured by the affinity reagent with the same efficiency as either the analyte or each other; the different internal reference species are each simply added to the analytical sample at concentrations which produce mass spectral signals that have the same amplitude as the signal that would be produced by a known concentration of the analyte.

With this bargraph mass spectrum, the analyte can be quantified in at least three ways: 1) by interpolating the analyte's mass spectral signal magnitude to the magnitude of the internal reference species mass spectral signal immediately above and below the analyte mass spectral signal, normally assuming a linear relationship between signal and concentration in this range, or 2) by estimating the analyte concentration by simple visual comparison of the analyte mass spectral signal and the nearest internal reference species signal (in magnitude) without computation, or 3) by certifying that the analyte signal, and therefore the analyte concentration, is above or below the signal level due to a reference species corresponding to a previously determined analyte concentration. This previously determined analyte concentration may be chosen to specify the presence or absence of a specific disease or condition. Since, under the bargraph strategy, the analyte is the certain antigen or certain antibody present in the specimen, the quantification of the analyte directly quantifies the certain antibody or certain antigen. The advantage of the bargraph approach is apparent in that the calibration scale is built into the mass spectrum giving exceptional immunity to instrumental and sample variations, and extremely rapid direct readout. For the most accurate analysis strategy (1) above is used, and the accuracy of this approach may be improved as necessary either by choosing the internal reference species concentrations to produce mass spectral signals which are closely spaced and near the analyte mass spectral signal, or by calibrating the analyte concentration range between those analyte concentration values specified by the internal reference species signals by using a number of standard preparations containing analyte concentrations within the concentration range to be calibrated.

The standard addition approach is another strategy for determining the relationship between the analyte/IRS signal ratio and the analyte/IRS concentration ratio. In this approach, separate calibration preparations are not required. Instead the effect on the analyte/IRS signal ratio of changing the concentration of the analyte in the analytical sample by a known amount is determined. Most directly, the analytical sample, to which an internal reference species has been added, is divided into several divided samples, at a minimum two. The first divided sample is mass spectrometrically immunoassayed and an analyte/IRS signal ratio determined from the resulting addition-absent mass spectrum. To the other divided sample or samples various known amounts of the analyte, or an analyte counterpart, are added to increase the concentrations of the analyte, or the analyte counterpart, by various known amounts. These samples similarly are mass spectrometrically immunoassayed resulting in a series of addition-present mass spectra from which the analyte/IRS signal ratios are determined.

The analyte/IRS signal ratios in the addition-present mass spectra are then used to determine the analyte concentration in the addition-absent sample. This is preferably done by using the addition-present analyte/IRS signal ratios closest in magnitude to the addition-absent analyte/IRS signal ratio to establish a mathematical relationship between changes in magnitude of the analyte/IRS signal ratio and the corresponding concentration change in the antibody or antigen due to the standard addition. This mathematical relationship may be expressed in a variety of ways, including but not limited to a line, a mathematical function, a graph, or computerized data. The standard addition mathematical relationship is then extrapolated to the intercept point for zero mass spectrometric response. The intercept point's value for standard addition concentration will be in negative units. The absolute value of this value inferentially represents the concentration of the analyte in the specimen.

Less preferably, a standard addition analysis may be performed in serial fashion without dividing the original sample. In this approach, the analytical sample, to which an internal reference species has been added, is mass spectrometrically immunoassayed using an incubation procedure designed to capture only a small fraction (for example, less than 5%) of the analyte and IRS, and an analyte/IRS signal ratio determined for this addition-absent sample. A known amount of analyte, or an analyte counterpart, is added to the original sample, increasing the concentration of the analyte, or analyte counterpart, by a known amount, and again the sample is mass spectrometrically immunoassayed using an incubation procedure designed to capture only a small fraction (for example, less than 5%) of the analyte and IRS. An analyte/IRS signal ratio is similarly determined for this addition-present sample. Further addition-present samples may be prepared by increasing the concentration of the analyte or analyte counterpart by further known amounts and these samples may be similarly mass spectrometrically immunoassayed to determine further analyte/IRS signal ratios.

The analyte/IRS signal ratios in the addition-present mass spectral signals are then used to determine the analyte concentration in the addition-absent sample exactly as in the parallel standard addition approach. Since mass spectrometric immunoassay of each addition-present sample serves to calibrate a sample in which the concentration of the analyte differs from the analyte concentration in the addition-free sample by an amount which depends on the amounts of analyte captured in the preceding mass spectrometric immunoassays, it is apparent that the accuracy of this procedure will only be acceptable if the amount of analyte captured in each successive step is small, for example if 5% of the analyte is captured in the mass spectrometric immunoassay of the addition-free sample and mass spectrometric immunoassay of a single addition-present sample is performed, the analyte concentration determined thereby would be in error by 5%.

The relative signal approach compares two analyte signals to each other where the concentrations of the analytes in the specimens are unknown. Often times the precise concentration of an antibody or antigen is not the information needed. Rather, knowing whether the antibody or antigen is present in levels at, below, or above the level of another antibody or antigen is what is needed. It is irrelevant whether a numerical figure is reached because only the relative relationship matters. To compare two or more analyte concentrations to each other by means of their mass spectrometric immunoassay responses, it is necessary only to know the relative response of the analytical process to each analyte, i.e., the relative amplitude of the mass spectrometric signals when each analyte is present in a calibration sample at identical concentrations (or at a concentration ratio which is known). In this strategy, a separate internal reference species is not required because each analyte serves to normalize the other, i.e., both analytes are subjected to identical affinity capture procedures and to identical mass spectrometric procedures.

The relative signal and simple ratio quantification methods share some similarities. Both compare the mass spectral signals of one analyte to another analyte. The two analytes can originate from one specimen, thus involving only one mass spectrum, or can each originate from separate specimens, thus involving two mass spectra. It is not necessary that the analytes have identical molar responses, i.e., affinity constants and desorption/ionization efficiencies.

It is apparent that either approach can be used for the quantification of more than two analytes and/or involve more than two specimens.

It is also apparent that the analytes from multiple samples may be the same type of analyte, or different. Therefore, the following descriptions are meant to include multiple specimens and/or multiple analyte immunoassays.

When two or more specimens are involved, both the simple ratio and relative signal quantification methods require that an internal reference species be present in each specimen sample in the same concentration to normalize the mass spectra. If one specimen is used, signals for the two analytes must be distinguishable in the mass spectrum, and no normalizing internal reference species is necessary. It is apparent that the two analytes whose mass spectral signals are being compared in a single sample are used to quantify either or both of the analytes and are essentially acting as analyte and an internal reference species, i.e., in qualitative and quantitative capacities at the same time. Therefore, to avoid confusion of terms, "internal reference species" is used in connection with the relative signal and simple ratio quantification methods to mean the antibody or antigen occupying the normalizer role. An "analyte" is used to mean the antigen or antibody acting in both a qualitative and quantitative role.

For relative signal quantification of analytes in separate specimens, the specimens (with internal reference species present) are each mass spectrometrically immunoassayed with an affinity reagent having an affinity for each antigen or antibody being looked for in that specimen. The resulting spectra are normalized, then a comparison of the analyte signals made to determine which analyte is of greater or lesser concentration. By way of illustration only, suppose two blood samples from the same person taken at different times are mass spectrometrically immunoassayed to determine whether there is a change in the level of antigen X. Affinity reagent having an affinity for antigen X would be used in the mass spectrometric immunoassay of both samples. The two mass spectra would each show a mass spectral signal for antigen X and the internal reference species. After normalizing the spectra, the two antigen X signals could be compared to see if the level of antigen X had dropped or risen in the intervening time between taking the samples. The absolute concentration of X in either sample can not be determined without further calibration, but the amplitude of the relative change may be determined.

In the simple ratio quantification strategy, two analyte mass spectral signals are compared where one of the analyte signals originates from a specimen where that analyte's concentration is known. Unlike the relative signal method above, a numerical quantification results. The unknown concentration analyte signal is calibrated against the known analyte mass spectral signal to determine the concentration of the unknown analyte in that specimen.

For simple ratio quantification of two analytes in the same specimen, the specimen is mass spectrometrically immunoassayed with an affinity reagent having an affinity for each antigen or antibody being looked for in that specimen. The resulting mass spectrum will contain a signal for each analyte which was present in the specimen. Where two signals result, calibration of the magnitude of the signal corresponding to the analyte of known concentration to the magnitude of the signal of the analyte of unknown concentration determines the concentration of the other.

To further aid in the understanding of the present invention, and not by way of limitation, the following examples are presented:

EXAMPLE 1

In one practice of the present invention, a single analyte, myotoxin a, was detected in human whole blood using the affinant, anti-myotoxin a, as a constituent of the affinity reagent, and then quantified using a working curve strategy. Myotoxin a is one toxin found in the venom of the prairie rattlesnake, *Crotalus viridis viridis* (*C. v. viridis*).

The antibody, anti-myotoxin a immunoglobulin IgG affinity purified from rabbit antiserum, was used to prepare the affinity reagent as follows. One milliliter of antibody solution (the solution contained the antibody at 5 mg/mL in 0.01 M tris[Hydroxymethyl] aminomethane, pH 8.2 (tris)) was incubated for two hours (gentle agitation at room temperature) with 1 mL of slurried 6% agarose beads on which protein A was supported. Following incubation, the beads were washed (3×1 mL tris) and allowed to react at room temperature with 500 μL of 0.02 M dimethylpimelimidate dihydrochloride prepared in 0.2 M triethanolamine (pH 8.2). The reaction was stopped after one hour by washing (3×1 mL) with 0.2 M triethanolamine followed by one milliliter 0.2 M sodium citrate buffer (pH 2.8). The reagent was finally washed (3×1 mL) with tris and resuspended in 500 μL of the same buffer.

Stock human blood (SB) was prepared after intravenous retrieval by immediately diluting to ten times volume with normal saline to prevent coagulation. Three specimens were prepared from this diluted stock blood by combining 50 μL SB, 150 μL tris and 2 μL aliquot of *C. v. viridis* venom at a concentration of 0.2 mg/Ml (resulting after dilution in a concentration of 0.002 mg/mL venom).

An internal reference species for the quantification of myotoxin a was prepared by lysine conversion of myotoxin a to homoarginine (H-myotoxin a). The lysine modification was carried out as follows: myotoxin a (final concentration=10 mg/mL) was dissolved in 0.5 M O-methylisourea, which was adjusted to pH 11.0 with 8.0 M NaOH. The solution was incubated at 4° C. for 120 hours. The reaction was stopped by addition of an equal volume of 1 M sodium dihydrogen phosphate at pH 5.0. The mixture was then desalted with an Amicon ultracentrifugation device fitted with a PM-2 membrane filter at 4° C. The resulting solution was lyophilized and stored for future use in a desiccator at −20° C. The modification resulted in the conversion of each of the ten lysine residues to a guanidinium group, giving a total shift in mass of 420 Da.

Three microliter aliquots of slurried affinity reagent were incubated for 45 minutes with a 200 μL volume of the specimen containing 0.002 mg/mL whole venom and 40 nM (nanomolar) H-myotoxin a. The affinity reagent, now containing myotoxin a affinity bound to the retained anti-myotoxin a, was then physically separated from the specimen by forcing the entire 200 μL (microliter) volume through the backside of a P-10, 10 μL filter pipette tip thereby retaining the affinity reagent on the filter. The affinity reagent was then washed by forcing rinses (2×1 mL 0.1% Triton X-100, 2×1 mL tris, 1 mL triply-distilled water) through the P-10 tip.

After the final rinse, four microliters of the MALDI matrix, ACCA (α-cyano-4-hydroxycinnamic acid saturated in 1:2, acetonitrile: 1.33%, aqueous trifluoroacetic acid), was drawn through the P-10 tips and over the retained affinity reagent thereby disassociating and enabling laser desorption/ionization of the myotoxin a and H-myotoxin a. The whole volume was then immediately driven out of the P-10 tip and placed directly onto a mass spectrometer probe tip and allowed to air-dry before insertion into the vacuum system of the mass spectrometer. The time required for sample preparation was approximately one hour.

Matrix-assisted laser desorption/ionization time-of-flight mass spectrometry of the dried material on the mass spectrometer probe tip was then performed on a linear time-of-flight mass spectrometer. The instrument consisted of a 30 kilovolt two-stage acceleration source followed by a 1.4-meter field free drift region containing a particle wire guide. A frequency-tripled Nd:YAG (355 nm) LUMONICS HY 400 laser was used for desorption/ionization. Ion signals were detected using a hybrid microchannel plate/discrete dynode electron multiplier and recorded using a 500 MS/s transient recorder (TEKTRONIX TDS 520A) capable of fast signal averaging. The laser irradiance was adjusted during signal averaging while monitoring the mass spectra on a sampling oscilloscope (TEKTRONIX TDS 310), in order to achieve optimum ion signal (significant signal versus maximum resolution). Time-of-flight spectrum was generated by signal averaging 50 laser shots into a single spectrum and transferring the data to an IBM compatible personal computer. Data was processed using the commercially available software, LABCALC (Galactic Industries). The time-of-flight mass spectrum was obtained in the positive ion mode and externally calibrated with a calibration equation generated using horse heart cytochrome c (molecular weight (MW) of 12,360 Da).

Figure 2:
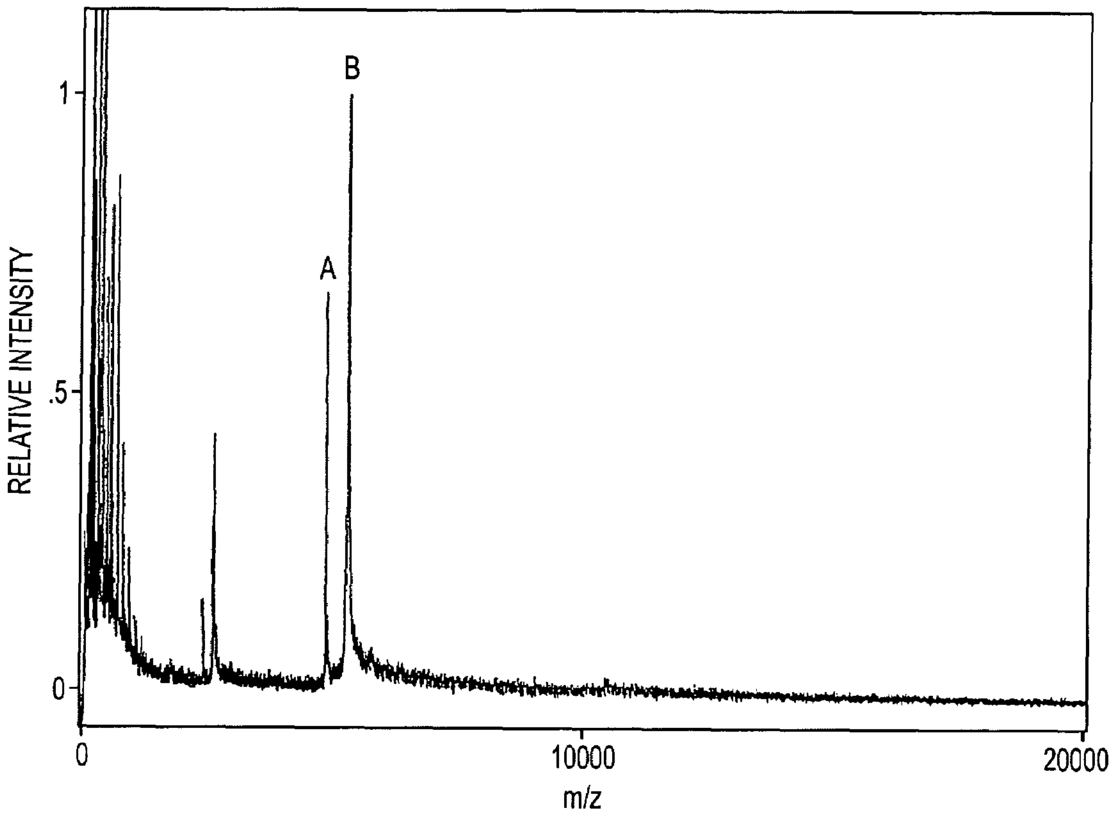
FIG. 2 is a mass spectrum resulting from the mass spectrometric immunoassay of the present invention of a venom-laced human blood sample for the antigen, myotoxin a, showing a distinct mass spectrometric response for singly charged myotoxin a at the mass/charge (m/z) ratio corresponding to the molecular weight of myotoxin a at 4,822 Da, and a second distinct response at the m/z ratio corresponding to 5,242 Da, which is the molecular weight of the modified variant H-myotoxin a, used as an internal reference species.

The resulting mass spectrum is reproduced in FIG. 2, clearly showing a mass spectral signal for myotoxin a at MW=4,822 Da., -A- and a mass spectral signal for the modified variant H-myotoxin a, at MW=5,242 Da., -B-.

Figure 3:
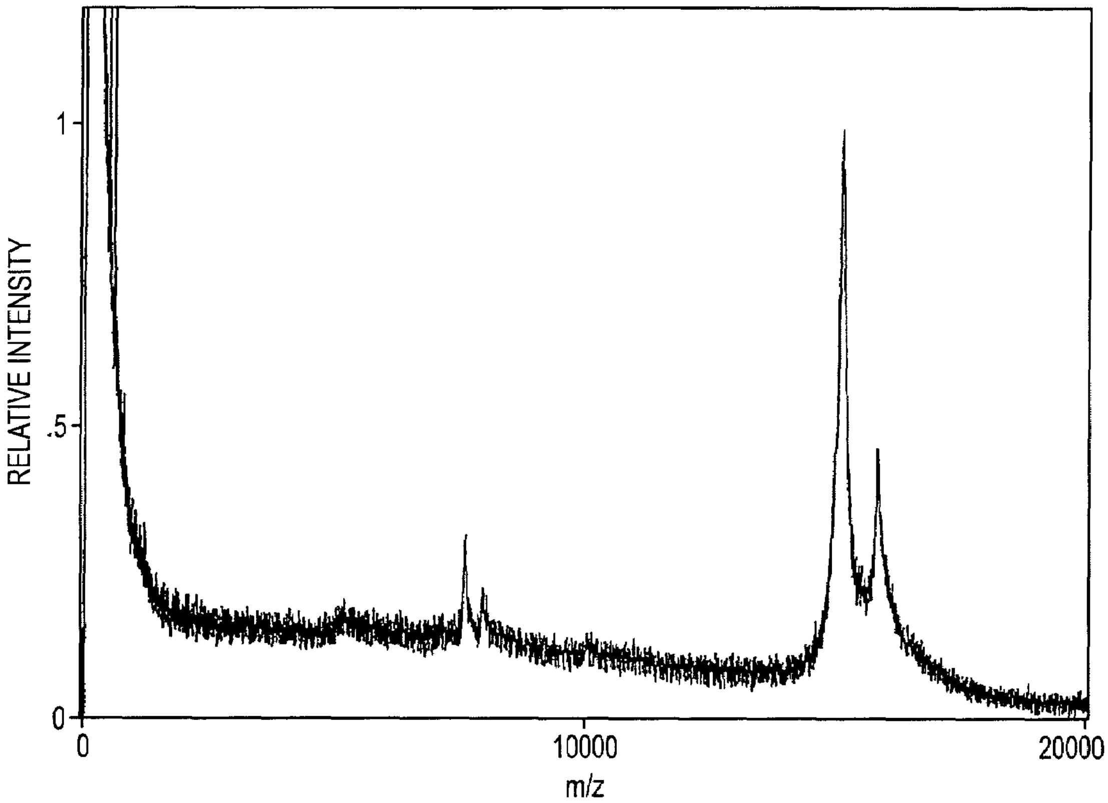
FIG. 3 is a mass spectrum resulting from mass spectrometric analysis, without affinity capture and isolation, of a venom laced human blood sample for the antigen, myotoxin a, showing no distinct mass spectrometric response at the molecular weight of myotoxin a, but rather showing a mass spectrometric response for singly charged hemoglobin A and B at the mass/charge (m/z) ratios corresponding to their respective molecular weights of about 16,000 Da.

A 200 μL volume of a second specimen containing 0.002 mg/ML of whole venom in human whole blood and 40 nM H-myotoxin like the first sample above, was mixed with the MALDI matrix, sinapinic acid (α-cyano-4-hydroxycinnamic acid saturated in 1:2, acetonitrile:1.33% aqueous trifluoroacetic acid), and placed on a mass spectrometric probe tip. After drying, the sample was then placed in a time-of-flight mass spectrometer and MALDI mass spectrometrically analyzed. The resulting mass spectrum is reproduced in FIG. 3 showing no signals for either of the myotoxin a species, rather, the mass spectrum is dominated by signals due to hemoglobin, i.e., hemoglobin A and B chain signals are observed at~16,000 Da (and doubly-charged at~8,000 Da). This example demonstrates the necessity of affinity capture and isolation prior to MALDI mass spectrometric analysis to detect myotoxin a.

The myotoxin a in the first specimen above containing 0.002 mg/mL of whole venom and 40 nM H-myotoxin a, was then quantified using a working curve strategy. Six preliminary samples which consisted of 50 μL SB, 150 μL tris, and 2 μL×0.02 mg/mL of the H-myotoxin a internal reference (40 nM in each sample) were prepared. To each preliminary sample an aliquot of either 5, 10, 20, 30, 40 or 50 μL of a purified myotoxin a solution (0.002 mg/mL) was added, resulting in a myotoxin a concentration range of 10 nM to 100 M. Each preliminary sample was then mass spectrometrically immunoassayed as was the first specimen except that three 50-laser shot mass spectra were acquired for each sample rather than one. A specimen containing 2 μL aliquot of *C. v. viridis* venom at a concentration of 0.2 mg/mL (resulting after dilution in a concentration of 0.002 mg/mL) was treated in the same manner.

Figure 4:
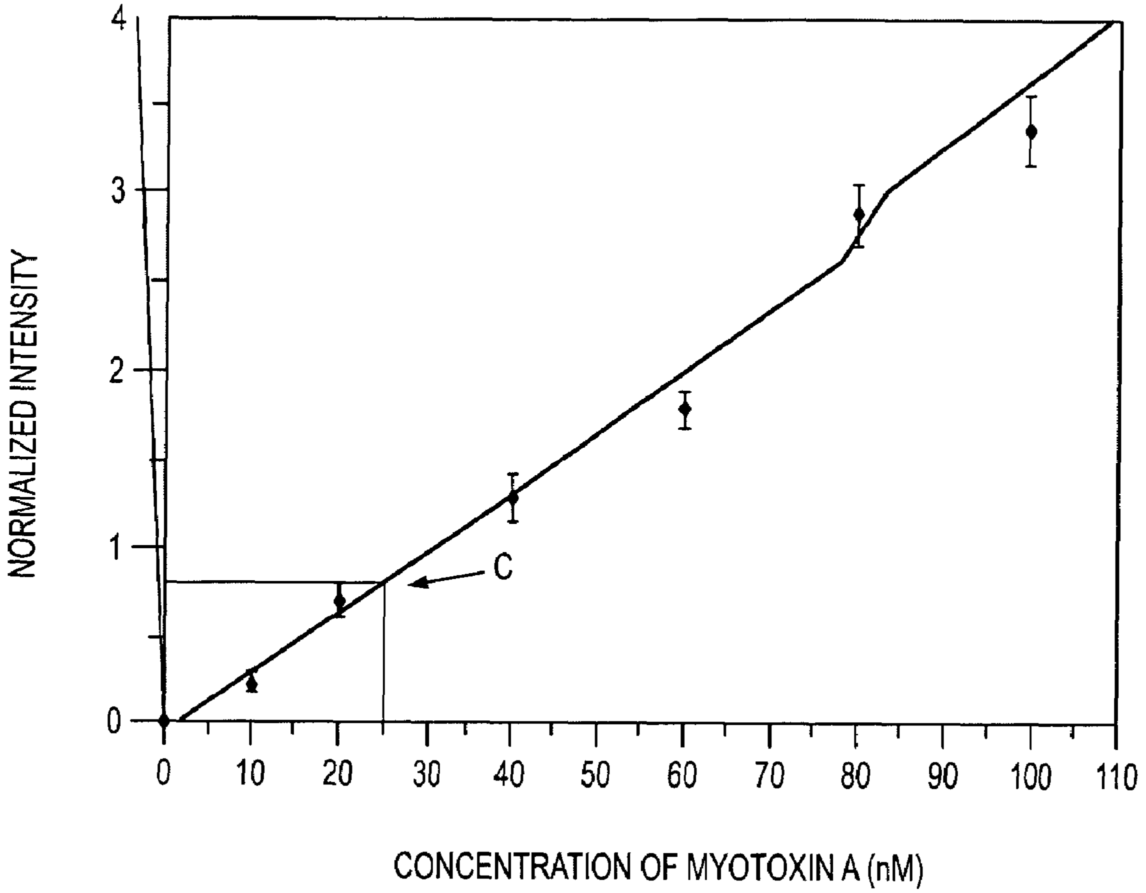

A six-point normal working curve was generated from the mass spectra data of the preliminary samples. The mass spectra of the specimen and all six preliminary samples were normalized to the signal intensity of the H-myotoxin a. The relative signal intensity of the myotoxin a in the preliminary samples (the average of the three spectra) was then plotted as a function of myotoxin a concentration thereby generating a six point working curve. FIG. 4 shows the working curve which relates the concentration of purified myotoxin a with the normalized signal intensity of the myotoxin a. Indicated at -5- is the normalized intensity observed for the specimen. The concentration of myotoxin a in the specimen was determined to be 25 nM.

EXAMPLE 2

Myotoxin a present in a blood sample containing 0.002 mg/mL of *C. v. viridis* venom was quantified employing the bargraph quantification strategy. Introduced into the sample were multiple internal reference species of myotoxin a which had been iodinated (at the tyrosine residues) using the following procedure: lodobeads (Pierce) were washed two times with 0.1 M sodium phosphate at pH 7.0, then incubated for five minutes with 0.4 M sodium iodide in a 0.1 M sodium phosphate solution at pH 7.0. An equal volume of myotoxin a, 2 mg/mL in buffer, was added to the sodium iodide/lodobead solution. Two lodobeads were used for each milligram of myotoxin a. The mixture was incubated overnight (~10 hours) at room temperature, after which the reaction was stopped by removal of the lodobeads. The modified protein was desalted and stored as described above. The reaction resulted in the production of four distinct iodinated species, with each addition incrementing the molecular weight of myotoxin a by 126 Da (the difference between the atomic weight of iodine and the atomic weight of the displaced proton). Immunoassay and mass spectral procedures were the same as described in Example 1.

Figure 5:
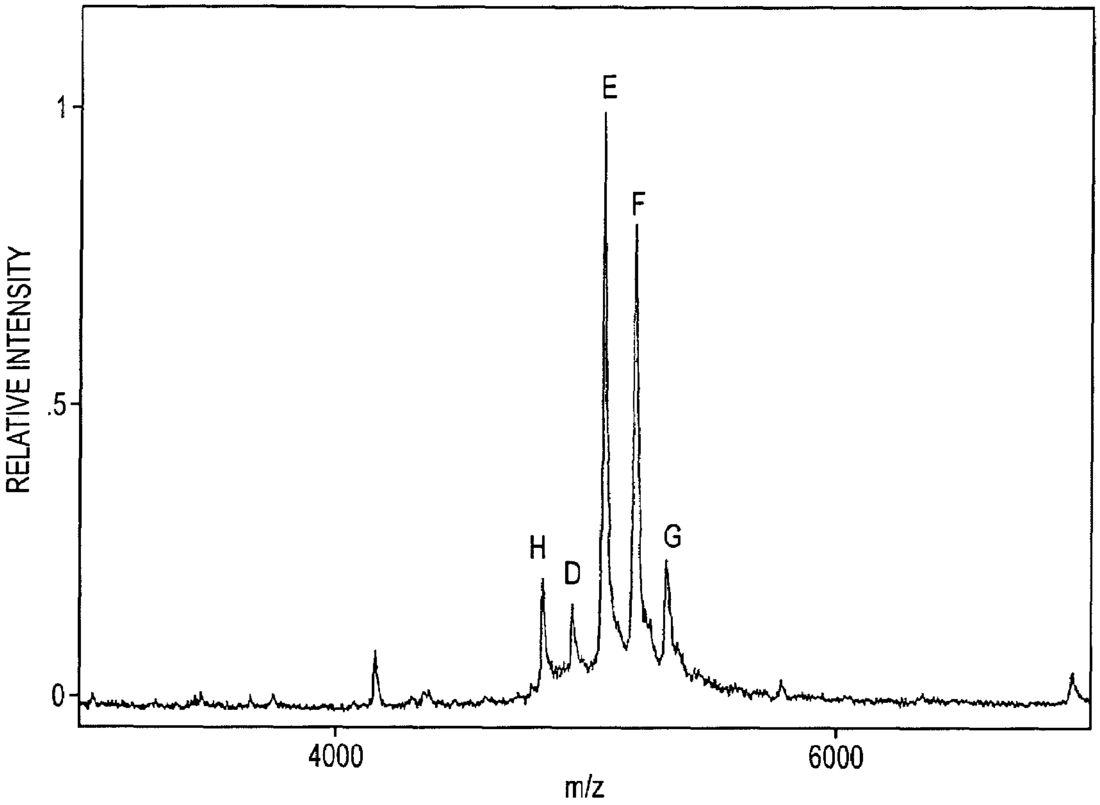

The internal reference species comprising the bargraph were calibrated against known concentrations of purified myotoxin a (using the calibration procedure described in Example 1). Once the relationships between the signal intensities of the myotoxin a and the internal reference species was established, the concentration of myotoxin a present in the sample could be determined, at a glance, by correlation with the internal reference peaks of closest intensity. For the example shown in FIG. 5, concentrations of 20, 100, 130 and 30 nM are indicated by the signal intensities of the first through fourth MV, -D-, -E-, -F-, and -G-, respectively. As the intensity of the myotoxin a signal -H- is observed to be between that of the first and fourth MV, it is determined that the myotoxin a concentration is in the range of 20 to 30 nM.

EXAMPLE 3

Figure 6:
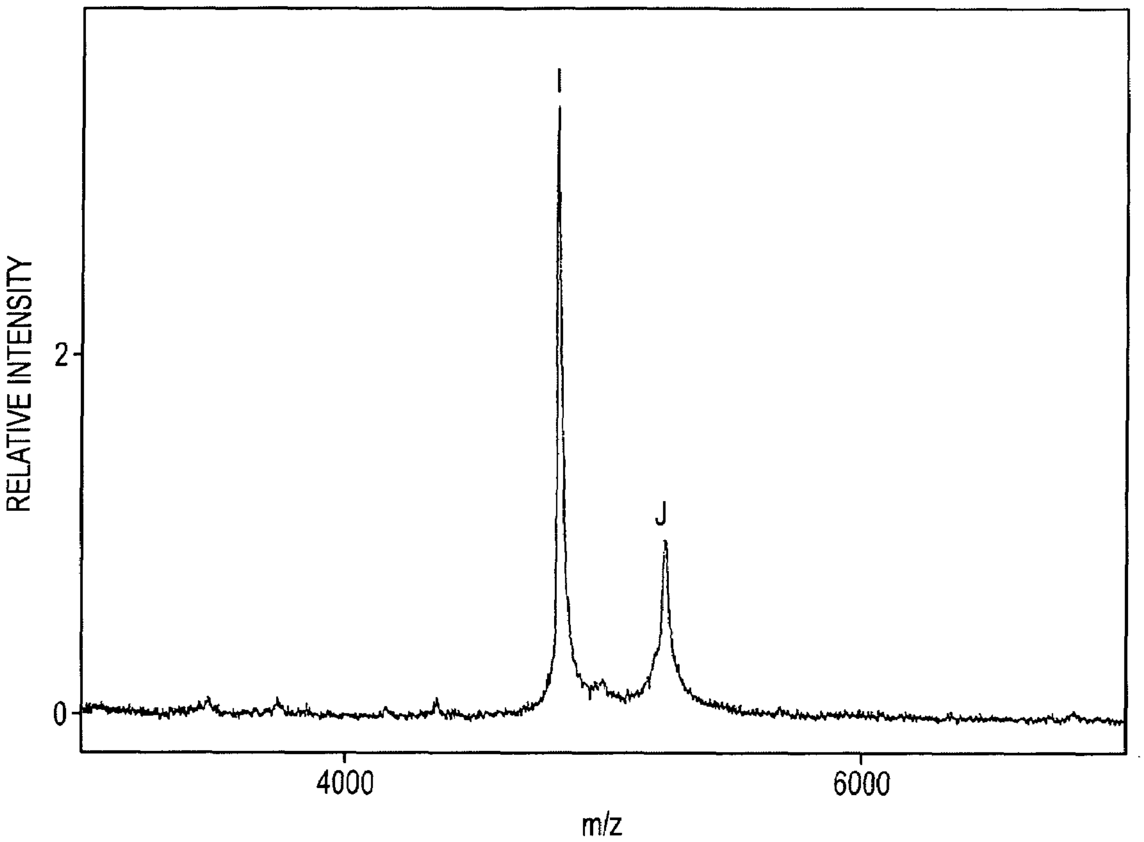

FIG. 6 demonstrates a single-point relative signal strategy for quantifying and detecting myotoxin a in human blood. A human blood sample containing an unknown concentration of myotoxin a and a 30 nM concentration of H-myotoxin a was prepared then mass spectrometrically immunoassayed according to the protocols of Example 1 above. The resulting mass spectrum shows mass spectral signals for myotoxin a, -I-, and H-myotoxin a, -J-, at their respective molecular weights. The relative mass spectrometric responses of myotoxin a and H-myotoxin a may be determined from the mass spectrum of FIG. 2 in which the concentrations of both species are known (25 nM myotoxin a, from the working curve calibration, and 40 nM H-myotoxin a). From this calibration it may be determined that equal concentrations of the two analytes give a 10% lower signal for H-myotoxin a. The myotoxin a signal is 3.5 times the H-myotoxin a signal for a known 30 nM concentration of H-myotoxin a. Therefore the myotoxin a concentration is calculated to be (30 nM×3.5/1.1) or 95 nM.

EXAMPLE 4

A multiplex mass spectrometric immunoassay was performed to simultaneously detect the presence of myotoxin a and Mojave toxin in human blood.

The protocols of Example 1 above were followed with two exceptions. First, anti-myotoxin a and anti-Mojave toxin basic subunit immunoglobulins IgG were immobilized on 6% agarose beads resulting in an affinity reagent containing antibodies towards both myotoxin a and Mojave toxin. Second, the specimens of human blood contained 0.002 mg/mL of the whole venom of the Mojave rattlesnake, *Crotalus scutulatus scutulatus* (*C. s. scutulatus*), rather than the venom of *C. v. viridis,* and the specimens did not contain the internal reference species, H-myotoxin a. The venom of the *C. s. scutulatus* contains both myotoxin a and Mojave toxin.

Figure 7:
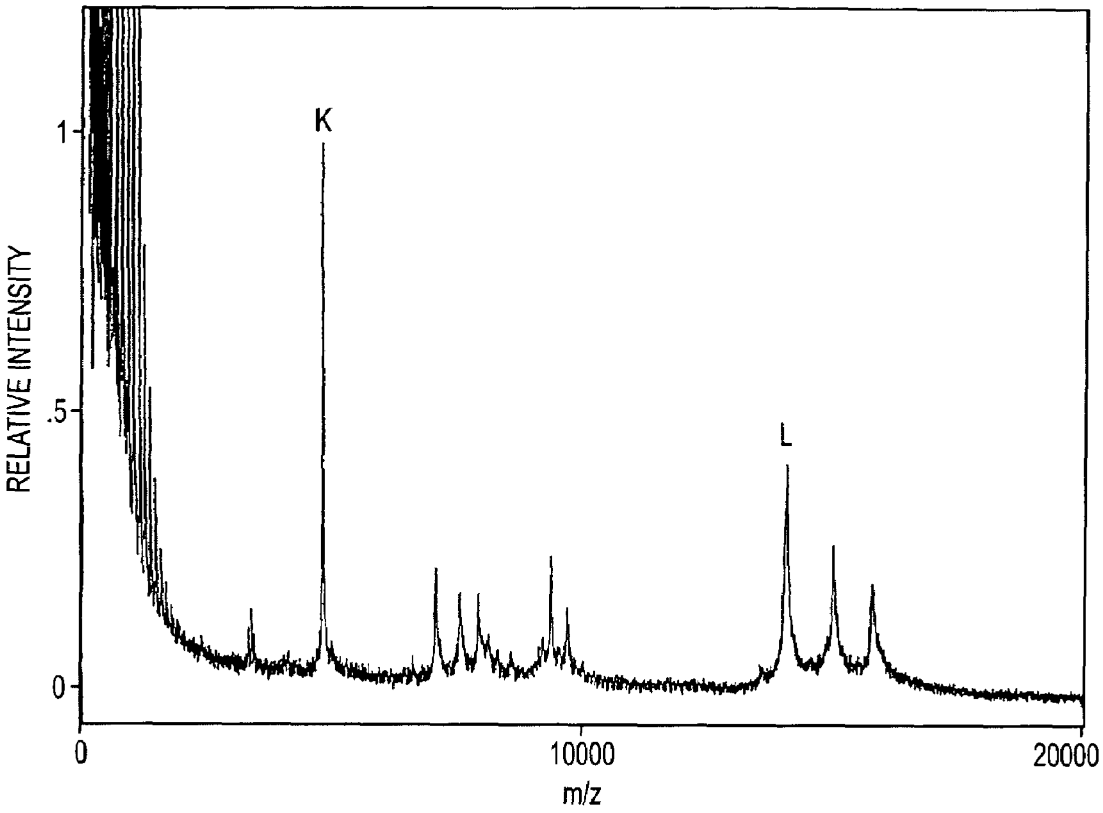
FIG. 7 is a mass spectrum resulting from the multiplex mass spectrometric immunoassay of the present invention of a venom laced human blood sample for myotoxin a and Mojave toxin showing distinct mass spectral signals for myotoxin a and Mojave toxin located at their respective molecular weights.

The mass spectrum resulting from the complete mass spectrometric immunoassay of a specimen is reproduced in FIG. 7, clearly showing a mass spectral signal for myotoxin a at MW=4,822 Da., -K-, and Mojave toxin at MW=14,175 Da., -L-. Also observed in the mass spectrum are signals due to the hemoglobin present in the blood sample (A- and B-chains at MW of ~16,000 Da). These did not prove a serious complication to the assay as the toxin signals are clearly observed at resolved values.

Mere MALDI mass spectrometric analysis of another identical specimen without affinity capture and isolation of myotoxin a and Mojave toxin yielded a mass spectrum with no discernable signals for the toxins similar to that shown in FIG. 3.

EXAMPLE 5

Example 5 demonstrates the detection and quantification of the blood serum protein a-1-acid glycoprotein (hence A1AG) using a mass spectrometric immunoassay in which the internal reference species is intrinsic to the biological system was performed. The internal reference species in this example is human serum albumin (hence HSA), another blood serum protein. A working-curve method was employed. The example was performed, to demonstrate principle, in a solution of normal saline.

Figure 8:
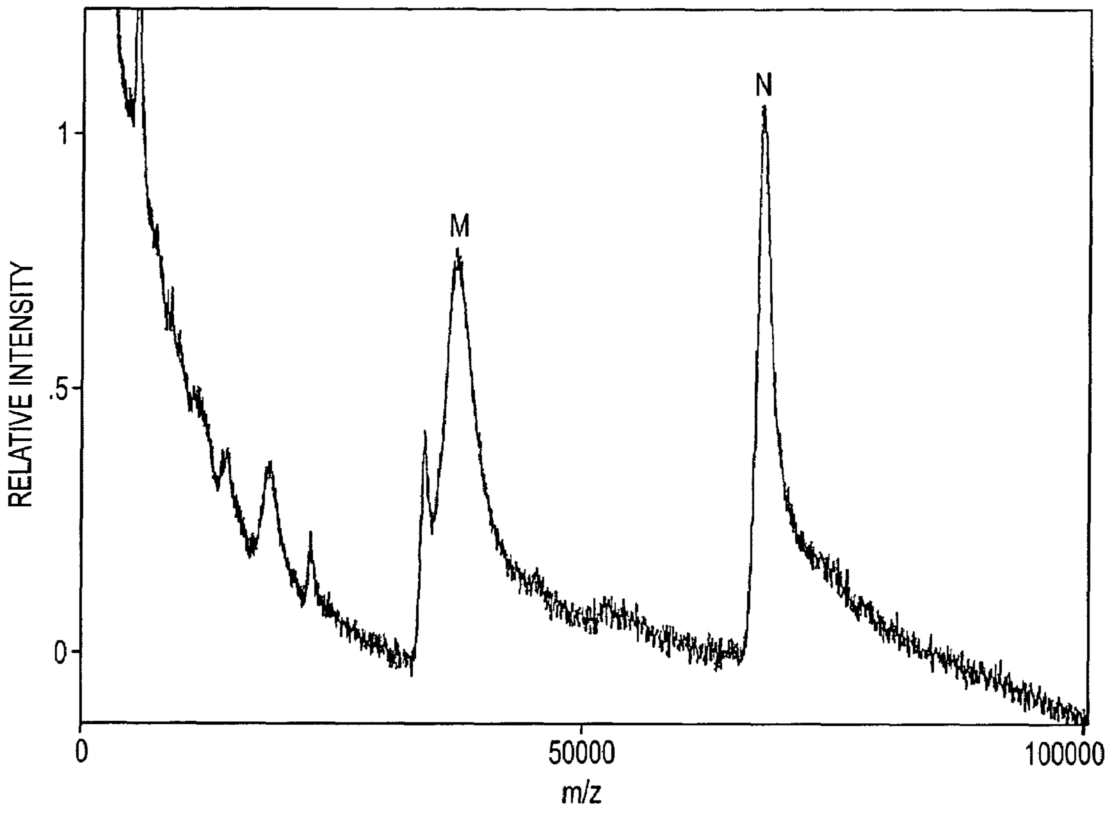
FIG. 8 results from the mass spectrometric immunoassay of the present invention of six preparation samples containing various concentrations of the antigen, α-1-acid glycoprotein (A1AG), and a constant concentration of the internal reference species, human serum albumin (HSA) and is a mass spectrum of one of these preparation samples, showing distinct signals for A1 AG at m/z~37,000 and for HSA at m/z~67,000.
Figure 9:
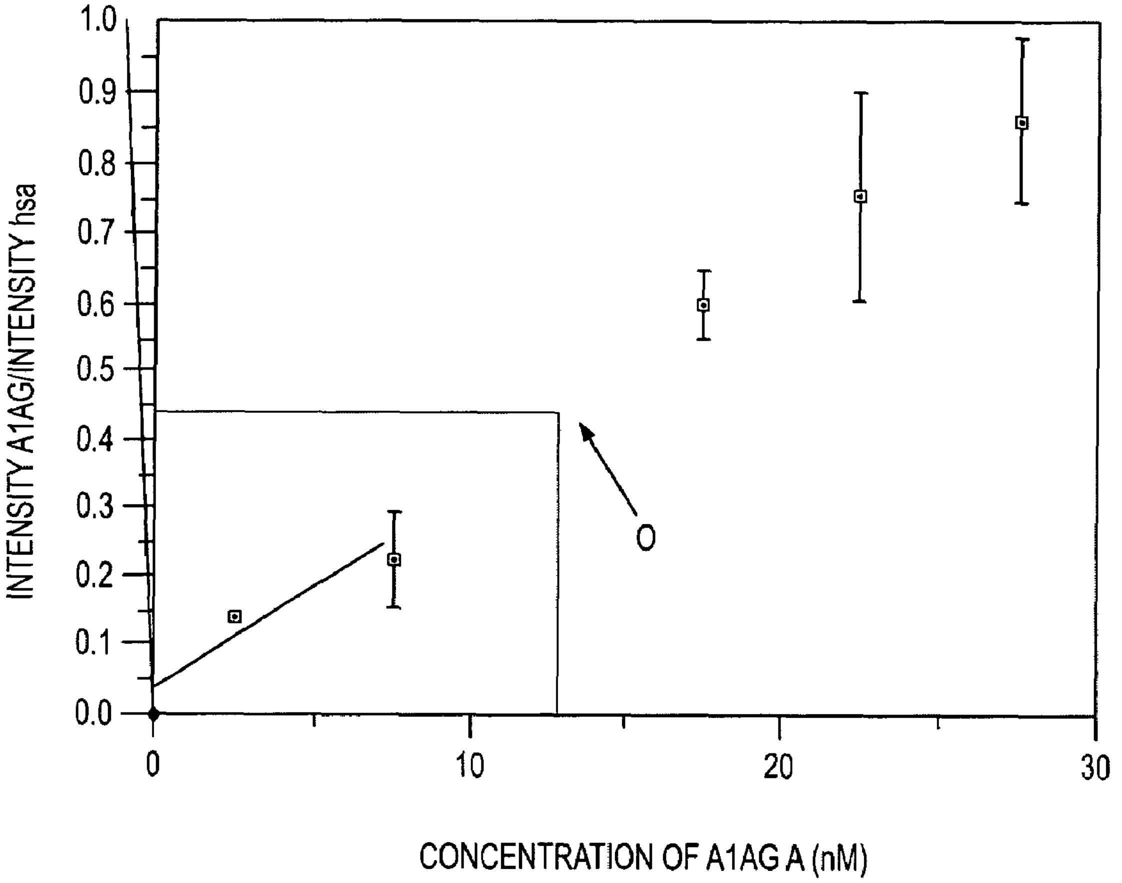
FIG. 9 is a working curve relationship between the concentration of α-1-acid glycoprotein (A1AG) in a specimen and the magnitude of the mass spectrometric response for α-1-acid glycoprotein, normalized with the internal reference species, human serum albumin.

Five preliminary samples were prepared containing a constant concentration of HSA to serve as the internal reference species, and also containing A1AG in the range of 2.5 nM to 27.5 nM. Each preliminary preparation was mass spectrometrically immunoassayed with a separate affinity reagent made of both an immobilized antibody to HSA and an immobilized antibody to A1AG. The resulting mass spectrum from one of the preliminary preparations (containing 27.5 nM A1AG) is shown in FIG. 8 with the HSA signal at -N- and the A1AG signal at -M-. All resulting mass spectra in this example were normalized to the HSA signal, and the normalized signal intensities of the A1AG were then used to construct the working curve depicted in FIG. 9.

An analytical sample, known to contain 12.5 nM A1AG was mass spectrometrically immunoassayed under similar conditions for the preparations above. The resulting A1AG signal was within that represented on the 5-point working curve of FIG. 9 and is shown at point -O- corresponding to an A1AG concentration of~12.5 nM which verifies the accuracy of the working curve quantification method.

EXAMPLE 6

The use of mass spectrometric immunoassay and the standard addition quantification strategy to detect and quantify myotoxin a in human blood laced with the venom of the Mojave rattlesnake, *C. s. scutulus* was performed. The venom of the Mojave rattlesnake contains both myotoxin a and Mojave toxin. The Mojave toxin intrinsic to the specimen is used in this example as an internal reference species to quantify myotoxin a.

Figure 10:
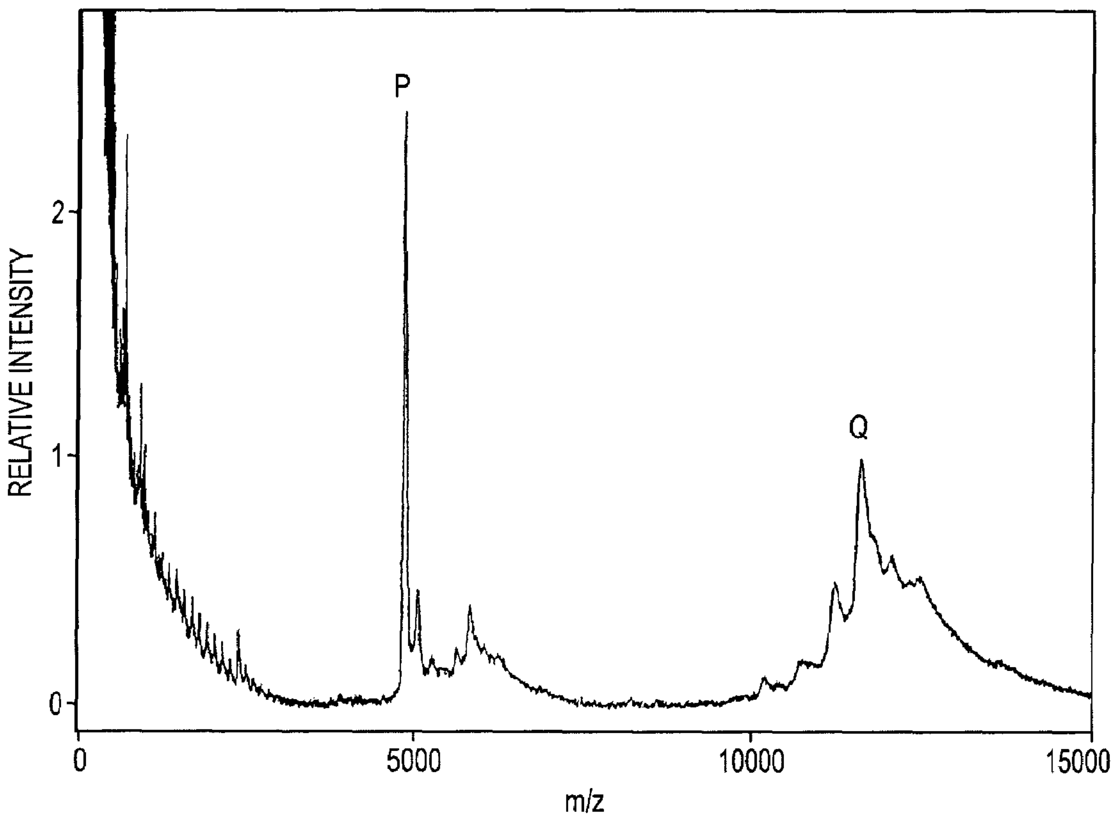
FIG. 10 results from the mass spectrometric immunoassay of the present invention of the rattlesnake toxin, myotoxin a, in human blood containing the venom of the Mojave rattlesnake, and to which various aliquots of purified myotoxin a have been added to allow quantification by the standard addition strategy, and shows a mass spectrum of a sample in which the concentration of myotoxin a was increased by 1250 nM over the intrinsic level.

A venom-laced blood sample was first divided equally amongst five separate containers. Aliquots of purified myotoxin a were added to each container, resulting in the samples possessing myotoxin a concentrations of 0, 180, 540, 890 and 1250 nM over that intrinsic to the sample. All five samples were then mass spectrometrically immunoassayed according to the protocols of Example 4 and the resulting mass spectra normalized to the Mojave toxin signals. FIG. 10 reproduces the results from the standard addition analysis in which myotoxin a was added at a concentration of 1250 nM over the intrinsic level. The signals for myotoxin a and Mojave toxin are observed at -P- and -Q-, respectively.

Figure 11:
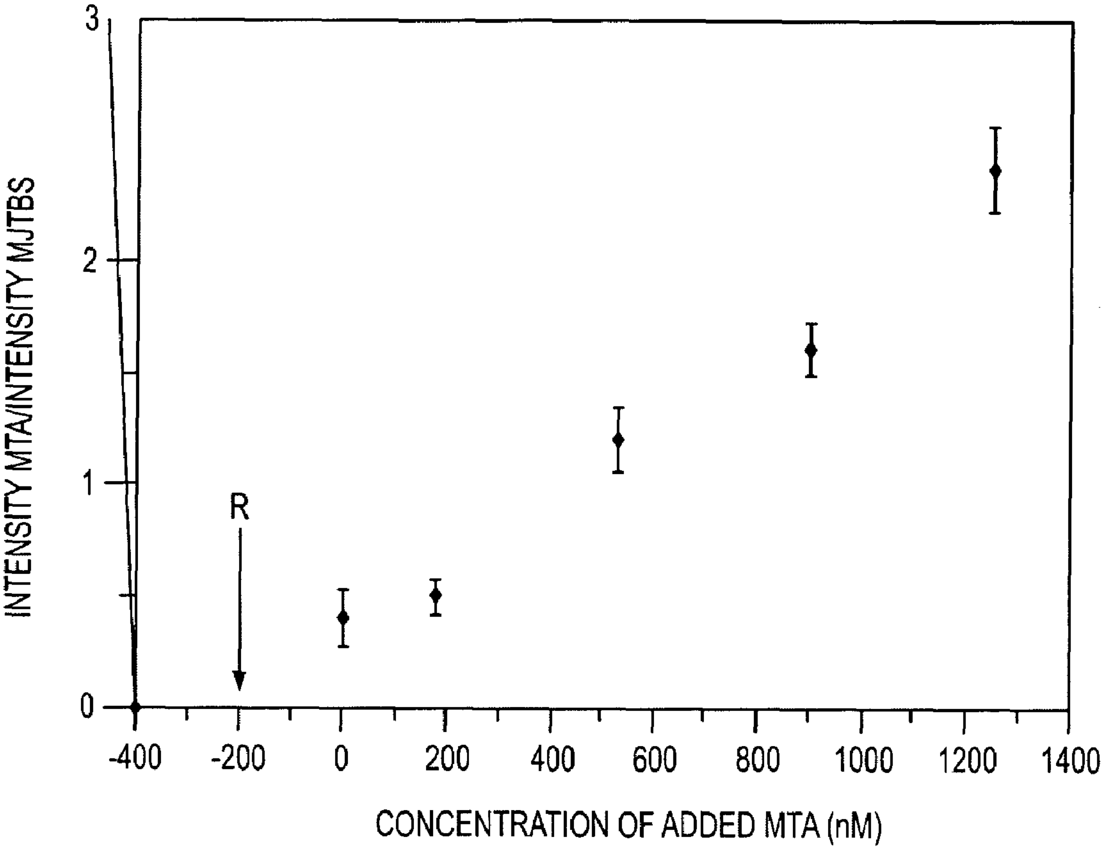
FIG. 11 is the standard addition line defining the relationship between added myotoxin a and the mass spectral responses for myotoxin a, normalized to the mass spectral response for another venom component, Mojave toxin, which is present in the blood sample at a constant concentration and consequently may be used as an internal reference species.

The normalized myotoxin a signals were then plotted as a function of the concentration of myotoxin a (added), and the points fit with a straight line as shown in FIG. 11. The standard addition line was then extrapolated to the baseline (concentration of added myotoxin a). The intercept point, -R-, indicated the concentration of myotoxin a intrinsic to the specimen to be 190 nM.

EXAMPLE 7

A multiplex mass spectrometric immunoassay was performed to detect myotoxin a and Mojave toxin in human blood. The myotoxin a was then quantified using the bargraph approach and the Mojave toxin was quantified using a working curve in which the doubly-iodinated species serves as an internal reference species. A venom laced blood sample and affinity reagent were prepared according to the protocols outlined in Example 1 with two exceptions: 1) the venom used to lace a human blood sample was that of *C. s. scutulatus,* and 2) two antibodies, anti-myotoxin a and anti-Mojave basic subunit, were present in the antibody solution used to prepare the affinity reagent.

Figure 12:
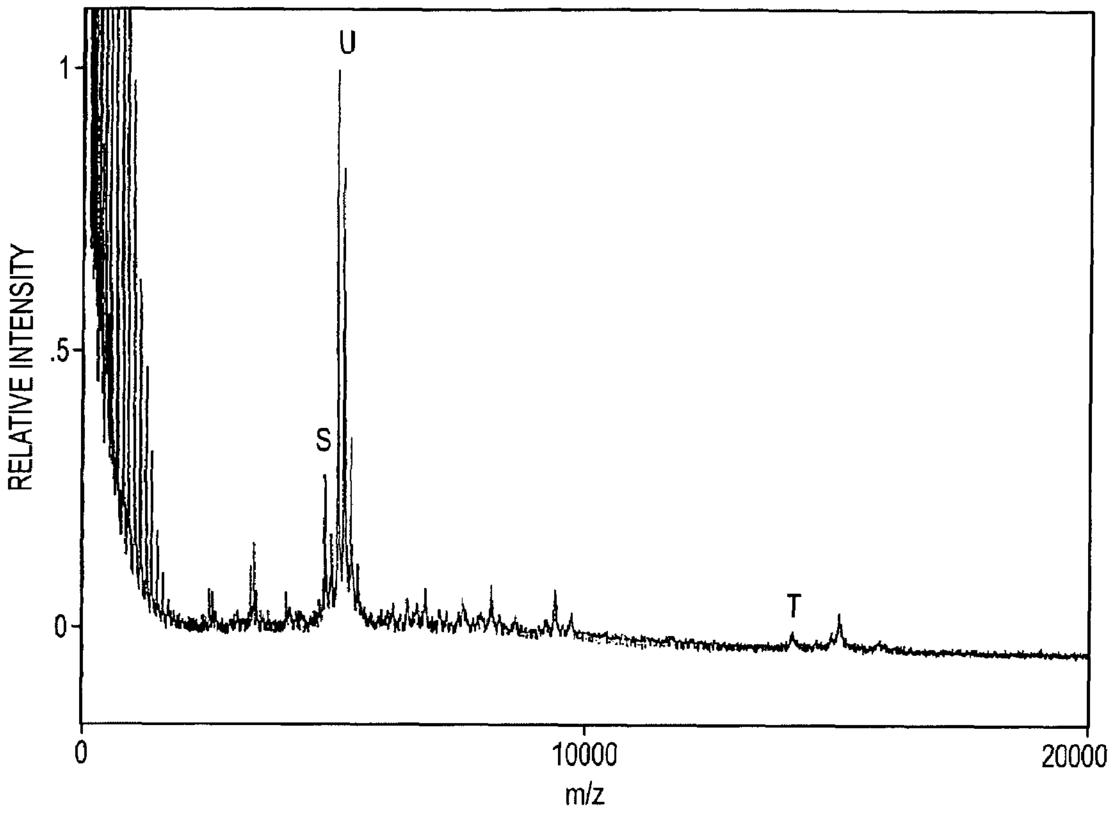
FIG. 12 is a mass spectrum of a venom laced blood sample containing five modified variants of myotoxin a resulting from the mass spectrometric immunoassay of the present invention in Example 7, demonstrating a bargraph quantification strategy.

The mass spectrometric immunoassay proceeded as outlined in Example 1 with the iodinated modified variants of myotoxin a described in Example 2 introduced into the sample as internal reference species. Calibration of the bargraph was as in Example 2 and the working curve as in Example 6 with the doubly-iodinated species of myotoxin a serving as the internal reference. The mass spectrum resulting from the analytical sample containing 0.001 mg/mL *C. s. scutulatus* is shown in FIG. 12. Mass spectral signals are observed at 4,822 Da, -S-, indicating the presence of myotoxin a, and 14,175 Da, -T-, indicating the presence of Mojave toxin basic subunit. The iodinated myotoxin a signals are also observed at~4,950-5,320 Da, -U-

The myotoxin a signal registered between that of the 1st and 4th iodinated species indicating a concentration between 2 and 3 nM. From the working curve it was determined that the Mojave toxin basic subunit concentration was 15 nM±2.5 nM.

EXAMPLE 8

The mass spectrometric immunoassay method of determining the presence of one or more specific antibodies in sera was performed. The method involves retrieval of a portion of the general antibody population present in a sample, and use of this portion to construct the affinity reagent. The affinity reagent is then screened with specific antigens. Antigens are retained by the affinity reagent if the specific antibody is present in the original sample, and will register in the mass spectrum (indicating the presence of the specific antibody).

The specimen was that of blood serum drawn from a rabbit immunized against the toxin, α-cobratoxin. The affinity reagent was prepared by mixing 25 μL of protein A supported on 6% agarose beads with a solution containing 50 μL of the serum and 50 μL of 0.01 M tris[Hydroxymethyl] aminomethane, pH 8.2 (tris)) and incubated for two hours (gentle agitation at room temperature). Following incubation, the beads were washed (3×100 μL tris) and allowed to react at room temperature with 50 μL of 0.02 M dimethylpimelimidate dihydrochloride prepared in 0.2 M triethanolamine (pH 8.2). The reaction was stopped after one hour by washing (3×100 μL) with 0.2 M triethanolamine followed by 100 μL of 0.2 M sodium citrate buffer (pH 2.8). The affinity reagent was finally washed (3×100 μL) with tris and resuspended in 50 μL of the same buffer.

Figure 13:
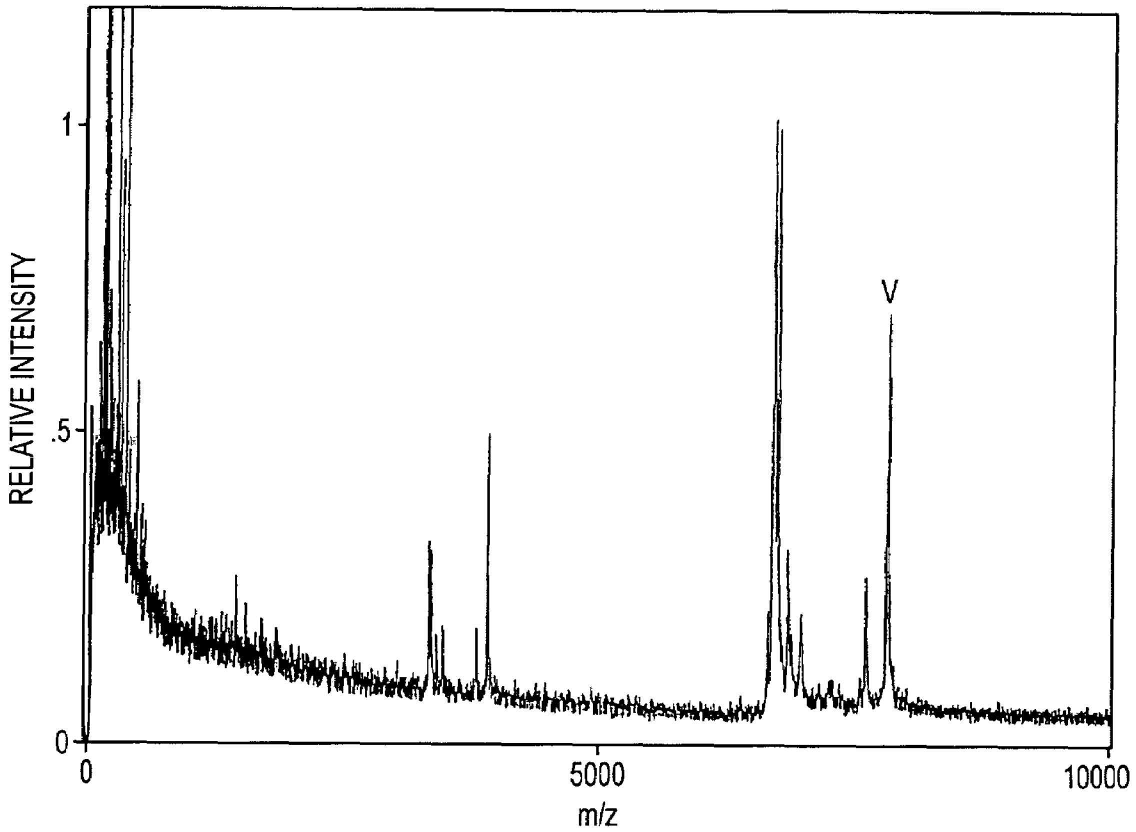
FIG. 13 is a mass spectrum resulting from mass spectrometric analysis of the preparation made of multiple antigen species in Example 7 showing responses at various m/z ratios characteristic of the various antigens.

A preparation containing multiple antigen species was prepared and MALDI mass spectrometrically analyzed. The resulting mass spectrum in FIG. 13 shows multiple signals corresponding to multiple antigens in the preparation. The singly charged signal for α-cobratoxin is identified at -V- at the molecular weight of 7,822 Da.

Figure 14:
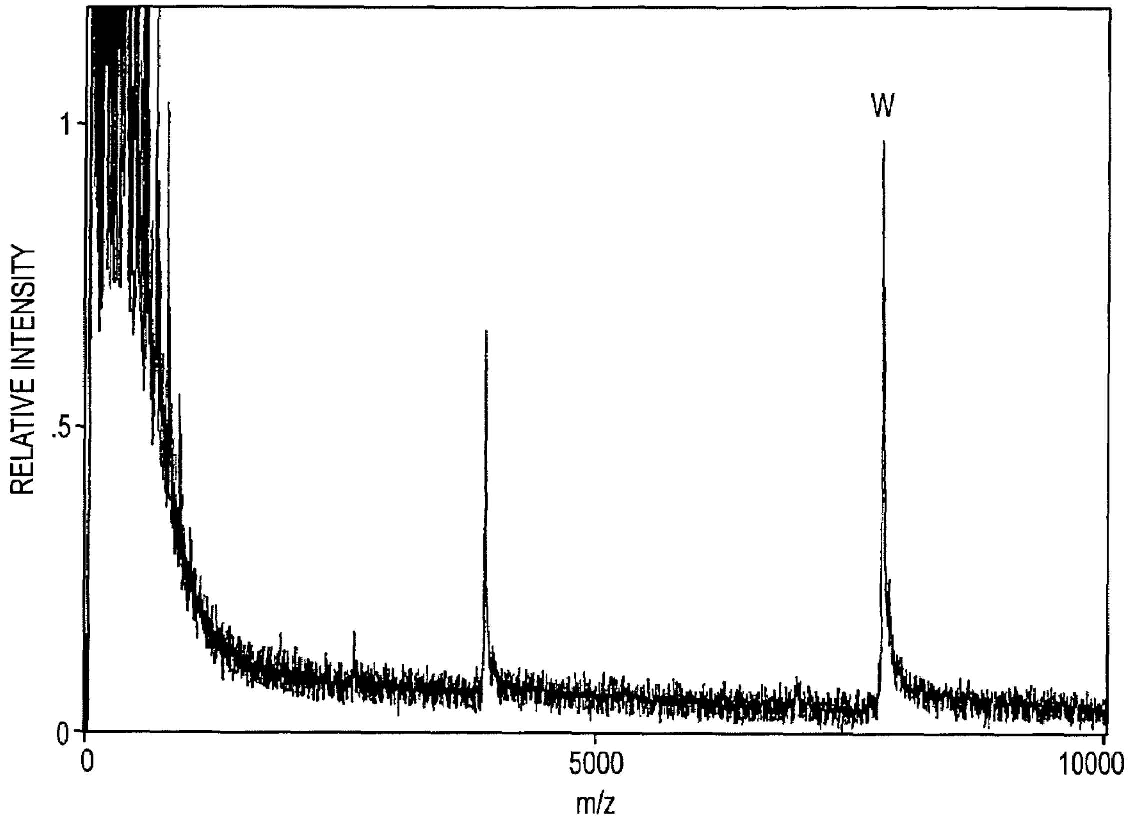
FIG. 14 is the mass spectrum of Example 7, showing a mass spectral response for the single antigen, α-cobratoxin, and demonstrating the third qualitative mass spectrometric immunoassay strategy of the present invention for inferentially detecting the antibody to α-cobratoxin in a specimen by capturing the antibody for α-cobratoxin and utilizing this antibody in the affinity reagent.

The affinity reagent was then incubated with the preparation following similar mass spectrometric immunoassay protocols already described to see which of the antigen species from the preparation of screening antigens were retained. The resulting mass spectrum is shown in FIG. 14. A signal at the mass-to-charge ratio of α-cobratoxin at 7,822 m/z (molecular weight 7,822 Da), -W-, indicates the retention of α-cobratoxin by the affinity reagent, which in turn indicates the presence of anti-α-cobratoxin present in the serum from which the affinity reagent was made.

From the foregoing, it is readily apparent that new useful embodiments of the present invention have been herein described and illustrated which fulfills all of the afore stated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. A method for separating a component of a specimen and analyzing the separated component comprising the steps of:

providing a tip having an affinity reagent present;

flowing a volume of specimen through the tip thereby binding the component of the specimen to the affinity reagent;

flowing an effective dissociation solution through the tip and over the retained affinity reagent with bound component, thereby eluting the bound component from the affinity reagent;

depositing the eluted component directly onto a mass spectrometer probe tip;

inserting the mass spectrometer probe tip into a mass spectrometer; and analyzing the eluted component by performing laser desorption/ionization of the eluted component.

2. The method of claim 1 wherein the dissociation solution is a MALDI matrix.

3. A method for separating a component of a specimen and analyzing the separated component comprising the steps of:

providing a tip having a filter contained therein;

binding a component of the specimen to an affinity reagent immobilized to a solid substrate;

forcing a volume of the affinity reagent with bound component into the tip, whereby the affinity reagent with bound component is retained by the filter within the tip, washing the retained affinity reagent with bound component by forcing rinses through the tip;

drawing a MALDI matrix through the tip and over the retained affinity reagent with bound component, thereby eluting the component from the tip;

depositing the eluted component and MALDI matrix directly onto a mass spectrometer probe tip;

inserting the mass spectrometer probe tip into a mass spectrometer, thereby enabling laser desorption/ionization of the component; and performing mass spectrometric analysis on the eluted component.

* * * * *